United States Patent [19]

Amidon et al.

[11] Patent Number: 4,685,918
[45] Date of Patent: Aug. 11, 1987

[54] LIPID OSMOTIC PUMP

[75] Inventors: Gordon L. Amidon, Ann Arbor, Mich.; Takeru Higuchi, Lawrence, Kans.; Jennifer B. Dressman, Ann Arbor, Mich.

[73] Assignee: Merck & Co., Inc., Rahway, N.J.

[21] Appl. No.: 697,105

[22] Filed: Feb. 1, 1985

[51] Int. Cl.$^4$ ............................ A61K 9/22; A61K 9/32
[52] U.S. Cl. ........................ 604/892; 427/2; 424/473
[58] Field of Search ............ 604/892; 427/2, 3; 424/19, 20, 22, 35

[56] References Cited

U.S. PATENT DOCUMENTS

| | | | |
|---|---|---|---|
| 3,854,480 | 12/1974 | Zaffaroni | 128/260 |
| 3,948,254 | 4/1976 | Zaffaroni | 128/127 |
| 3,995,632 | 12/1976 | Nakano et al. | 128/172 |
| 4,111,202 | 9/1978 | Theeuwes | 424/19 |
| 4,350,271 | 9/1982 | Eckenhoff | 128/260 |
| 4,522,625 | 6/1985 | Edgren | 424/19 |

FOREIGN PATENT DOCUMENTS 0010876  5/1980  European Pat. Off. .

Primary Examiner—John Kight
Assistant Examiner—Nathan Nutter
Attorney, Agent, or Firm—Joseph F. DiPrima; R. Brent Olson

[57] ABSTRACT

The instant invention is directed to a lipid osmotic pump, comprising:
(A) a core, comprising:
  (i) a beneficial amount of at least one substantially water insoluble active agent which is lipid soluble and/or lipid wettable;
  (ii) a sufficient amount of at least one water immiscible lipid carrier, which is liquid at the temperature of intended use, to dissolve and/or suspend said active agent; and
  (iii) a sufficient amount of at least one osmotic agent to ensure release of said lipid carrier from the pump; and
(B) surrounded by a water insoluble wall:
  (i) having a thickness of about 1 to 1000 microns;
  (ii) which is preferentially wetted by said lipid carrier over an aqueous solution of said osmotic agent;
  (iii) having a water permeability of about $1 \times 10^{-18}$ to $4 \times 10^{-15}$ cm$^3$ sec/g;
  (iv) prepared from at least one polymer permeable to water but substantially impermeable to said osmotic agent; and
  (v) having a means for said active agent and lipid carrier to be released through said water insoluble wall.

19 Claims, 28 Drawing Figures

LIPID OSMOTIC PUMP

BACKGROUND OF THE INVENTION

U.S. Pat. Nos. 4,350,271 and 3,995,632 describe dispensers that either absorb water and swell to dispense a lipophilic fluid or osmotically imbibe water to push a movable barrier which, in turn, dispenses a fluid which is liquid at temperature of use. Thus both inventions are similar in that lipophilic fluid is dispensed by means of a pressure generated by the interaction of water with a swellable polymer or with an osmotic agent. The instant invention is similar in function to these dispensers in that it also dispenses a lipid carrier by means of water imbibement and interaction with an osmotic agent. However, the instant invention is much different in structure and in mechanism of operation from these patented dispensers: (1) the osmotic agent and the lipid carrier are preferably present as a uniform mixture rather than being separated by a movable barrier or being present as separate layers, (2) the lipid carrier is preferentially released over the osmotic agent by means of preferential wetting of the inner surface of the polymeric wall by the lipid; intimate contact of the lipid carrier with the polymeric wall is aided by interfacial tension differences between the lipid carrier and the osmotic agent solution, formed by dissolution of the osmotic agent in the imbibed water; the lipid carrier is released through orifices or pores in said polymeric wall; and (3) the osmotic agent is released, secondary to the lipid carrier, whereas the swellable polymer and osmotic agent in the above-mentioned patented dispensers remain within the devices. The present invention thus has the advantage of being capable of releasing active agents in sequence, the first being released in the lipid carrier and the second being released in the osmotic agent solution. An active agent may, in fact, serve as the osmotic agent in this case. The instant invention can be easily configured in the form of tablets, devices, multiparticulate based dosage forms, and the like. Because of these unique properties, the instant invention having the ability to release active agents in sequence allows it to be utilized in a wider variety of applications in the controlled release of these agents.

The osmotic pump of the instant invention has the advantage that it is easier to make.

The present invention concerns an osmotically activated system for dispensing beneficial, preferably pharmacologically, active agents which have poor solubility in water. The system comprises an inner core compartment of active agent(s), lipid carrier(s) and osmotic agent(s) preferably in admixture, surrounded by an enclosing wall material. The core has the property that at the temperature of use, body temperature for pharmaceutical applications, the lipid carrier is or becomes fluid, and retains the active agent in a dissolved or suspended state. The wall consists of one or more polymer layers with the innermost layer being preferentially wetted by the lipid over the aqueous solution of osmotic agent(s). The wall constitutes a layer that is permeable to water and may or may not contain a permeability modifier and/or plasticizer. The lipid carrier containing the active agent is released from the system either via holes and/or pores in the wall as a result of water imbibition through the wall into the inner core compartment; the rate is controlled by the wall composition and dimensions. Sufficient osmotic agent is present to insure complete pumping of the lipid carrier at a controlled rate.

The object of this invention is to provide, for pharmaceutical applications, an osmotically activated system for the controlled delivery of pharmacologically active agents to the biological receptor sites over periods of time of preferably from 1 hour to several weeks.

The wall is the critical feature of the invention, not only providing a programmable fluid transport for controlled release of agent but the inner wall is preferentially wetted by the lipid carrier over the aqueous solution of osmotic agent(s) such that the lipid phase is pumped before the aqueous phase.

The preferential wetting of the wall by the lipid carrier provides a sufficient interfacial tension to prevent release of the aqueous phase until the lipid carrier has been pumped.

The wall may be composed of either insoluble, non-erodible materials mixed with leachable additives, or bioerodible materials containing leachable additives. Bioerodible materials would be selected to bioerode after a predetermined period with bioerosion occurring subsequent to the period of agent release.

Another object of the invention is to provide an osmotic system that is readily manufacturable to deliver a pre-determined dose of active agent(s) at a programmed rate from compositions of matter in the varied geometries and sizes of tablets, pellets, multiparticulates, and such related dosage forms as familiar to those skilled in the art of oral, buccal, vaginal, rectal, nasal, ocular, aural, parenteral and related routes of administration.

The key to the instant invention is not in the selection of the active agent(s) to be incorporated into the lipid, other than that it be substantially water insoluble and lipid soluble and/or lipid wettable. Likewise the key to the invention is not in the selection of the osmotic agent. The keys to the instant invention are the use of a water immiscible lipid carrier, which is liquid at the temperature of use, in particular body temperature, and in the specifications of the water insoluble wall.

A BRIEF DESCRIPTION OF THE DRAWINGS

DESCRIPTION OF THE INVENTION

Figure 1:
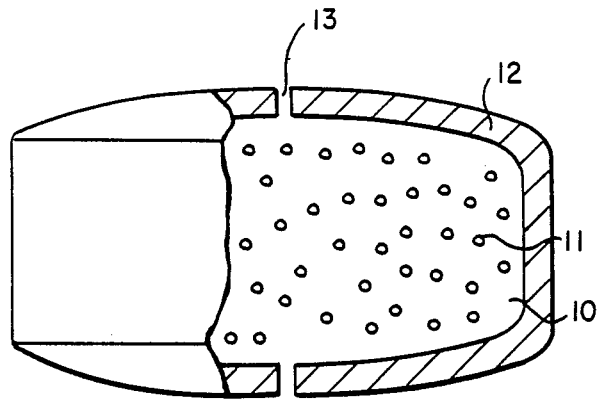
FIG. 1 is a cutaway of a single coated lipid osmotic pump having two holes through the wall.

The instant invention is directed to:
(A) a core, comprising:
  (i) a beneficial active amount of at least one substantially water insoluble active agent which is lipid soluble and/or lipid wettable;
  (ii) a sufficient amount of at least one water immiscible lipid carrier, which is liquid at the temperature of intended use, to dissolve and/or suspend said active agent; and
  (iii) a sufficient amount of at least one osmotic agent to ensure release of said lipid carrier from the pump; and
(B) surrounded by a water insoluble wall:
  (i) having a thickness of about 1 to 1000 microns;
  (ii) which is preferentially wetted by said lipid carrier over an aqueous solution of said osmotic agent;
  (iii) having a water permeability of about $1 \times 10^{-18}$ to $4 \times 10^{-15}$ cm$^3$ sec/g;
  (iv) prepared from at least one polymer permeable to water but substantially impermeable to said osmotic agent; and
  (v) having a means for said active agent and lipid carrier to be released through said water insoluble wall.

The expression "active agent" as used herein broadly includes any compound, or mixture of compounds, that can be delivered from the system to produce a beneficial result. The agent generally should be sufficiently insoluble in water or buffered solution such that less than about 10% of the drug partitions into the aqueous phase throughout the time of lipid release. By the phrase "lipid soluble and/or lipid wettable" is meant that the active agent remains associated with the lipid carrier rather than the solution of the osmotic agent.

The active agent includes pesticides, herbicides, germicides, biocides, algicides, rodenticides, fungicides, insecticides, antioxidants, plant growth promoters, plant growth inhibitors, preservatives, disinfectants, sterilization agents, catalysts, chemical reactants, fermentation agents, food supplements, nutrients, cosmetics, drugs, vitamins, sex sterilants, fertility inhibitors, fertility promoters, air purifiers, microorganism attenuators, and other agents that benefit that environment of use. Drugs are preferred.

As used herein, the term "drug" includes any physiologically or pharmacologically active substances that produce a localized or systemic effect in man or animals, which term includes domestic household, sport or farm animals such as sheep, goats, cattle, horses and pigs, for administering to laboratory animals such as mice, rats and guinea pigs, and to fishes, to avians, to reptiles and zoo animals. The term "physiologically" as used herein denotes the administration of drug to produce normal levels and functions. The terms "beneficial" and "pharmacologically" denote variations in response to amounts of drug including therapeutics: *Stedman's Medical Dictionary*, 1966, published by Williams & Wilkins, Baltimore, Md.

The phrase "drug formulation" as used herein means the drug is in the core dissolved in or suspended in the lipid carrier. The active drug that can be delivered includes inorganic and organic compounds without limitation, including drugs that act on the peripheral nerves, adrenergic receptors, cholinergic receptors, nervous system, skeletal muscles, cardiovascular, smooth muscles, blood circulatory system, synaptic sites, neuroeffector junctional sites, endocrine and hormone systems, immunological system, reproductive system, skeletal system, hormone systems, alimentary and excretory systems, inhibitory of hormonal and histamine systems, those materials that act on the central nervous system such as antidepressants, including amiflamine, amitriptyline, alaproclate, protriptyline, doxepin, imipramine, trazedone, maprotiline, zimelidine, fluvoxamine; antipsychotic-neuroleptic agents such as chlorpromazine, haloperidol, thioridazine, trifluoperazine, MK-0212, remoxipride; anticonvulsants such as carbamazepine, phenytoin, phenobarbital; sedative-hypnotic agents such as triazolam, chlordiazepoxide, temazepam, chlorazepate, alprazolam, diazepam, flurazepam, lorazepam, oxazepam, hydroxyzine, prazepam, meprobamate, butalbital, orphenadrine, chlorzoxazone, cyclobenzaprine; antiparkinson agents such as benztropine, carbidopa, levodopa, L 647,339; analgesics such as acetaminophen, oxycodone, hydrocodone, codeine, propoxyphen. Respiratory agents including sympathomimetics, brochodilators, antihistamines, and antiasthmatics such as diethylpropion, ephedrine, epinephrine, isoproterenol, metaproterenol, terbutaline, cyproheptadine, azatadine, diphenhydramine, promethazine, chlorpheniramine, brompheniramine, aminophylline, theophylline, albuterol, tranilast, enprofylline, budesonide may also be used. Cardiovascular and antihypertensive agents including coronary vasodilators, cardiac glycosides, beta-blockers, slow calcium channel blockers, antiarrhythmics, peripheral vasodilators, and agents for Pheochromocytoma such as isosorbide dinitrate, nitroglycerin, dipyridamole, digoxin, nadolol, propranolol, metaprolol, atenolol, timolol, disopyramide, procainamide, nifedipine, quinidine, lidocaine, diltiazam, verapamil, prazosin, clonidine, hydralazine, methyldopa, captopril, metyrosine, enalapril, lysinopril, felodipine, tocainide may also be used. Diuretics such as amiloride, spiranolactone, hydrochlorothiazide, chlorothiazide, acetazolamide, chlorthalidone, metolazone, furosemide, triamterene, methyclothiazide, ethacrynic acid, indacrinone; antiartereosclerotic agents such as mevinolin; hormones and steroids including estrogens such as conjugated estrogens, estradiol, ethinyl estradiol, diethylstilbesterol; progestins such as progesterone, hydroxyprogesterone, medroxyprogesterone, norethindrone; glucocorticoids and mineralocorticoids such as hydrocortisone, betamethasone, dexamethasone, methylprednisolone, prednisolone, prednisone, triamcinolone, and MK-0621 may also be used. Nonsteroidal anti-inflammatory agents, antiarthritic and antigout agents such as allopurinol, aspirin, fenprofen, ibuprofen, indomethacin, naproxen, phenylbutazone, sulindac, tolmetin, diflunisol, piroxicam, meclofenamate, penicillamine, probenecid, and colchicine; gastrointestinal agents including anticholinergics, antispasmodics, antidiarrheal, and antiulcer histamine-$H_2$-antagonists such as bethanechol, clidinium, dicycloine, meclizine, prochlorperizine, trimethobenzamide, loperamide, cimetadine, ranitidine, diphenoxylate, famotidine, and omeprazole; oral hypoglycemics such as chlorpropamide, tolazamide, and tolbutamide; anticoagulants such as warfarin, phenindione, and anisindione; anti-infective agents including antibiotic, antimicrobial, antiviral, antiparasitic, and antifungal agents such as cefoxitin, thiabendazole, cephalexin, tetracycline, ampicillin, amoxicillin, sulfamethoxazole, cefaclor, erythromycin, penicillin, nitrofurantoin, minocycline, doxycycline, cefadroxil, miconazole, phenazopyridine, norfloxacin, clorsulon, fludalanine, pentizidone, cilastin, phosphonomycin, ivermectin, imipenem, arprinocid, and foscarnet; nutritional supplements including vitamins such as isotretinoin (Vit. A), cholecalciferal (Vit. D), tocopherols (Vit. E), and phytonadione (Vit. K); amino acids such as L-tryptophan and L-lysine; and lipids such as corn oil and medium chain triglycerides may also be used.

The drug can be prepared in various forms to be suitable for use herein such as esters of acids or alcohols and amides. Also a drug that is water soluble can be chemically modified to make it less water soluble and more lipid soluble. Such drugs or complexes can be delivered from the device and can be converted by enzymes, hydrolyzed by body fluids or other metabolic processes to a biologically active form. The agent can be in the core as a solution, dispersion, particle or powder. Generally, the device can house from 1 μg to 5 grams or more, with individual devices containing for example 1 μg, 1 mg, 5 mg, 500 mg, 1 g and the like. However, any beneficially or pharmacologically active amount is sufficient in the case of drugs.

The expression "lipid carrier" as used herein broadly includes any compound, or mixture of compounds, that is not miscible with water and which is a fluid at the temperature of intended use, body temperature in the case of drugs. This includes triglycerides and triglyceride mixtures that are commonly used as suppository bases which are solid at room temperature but melt at body temperature such as cocoa butter, hard butter and commercially available materials sold under the trade names of Witepsol ®, Suppisere ® and Hydrokote ® suppository bases. Also included are hydrocarbons and hydrocarbon mixtures such as mineral oil, petrolatum-mineral oil mixtures, saqualine and fluorocarbons. Also included are fatty acids such as oleic acid and esters such as isopropyl myristate, isopropyl palmatate. Witepsol ® suppository bases (manufactured by Dynamit Nobel Chemicals) are glycerol esters of mixtures of saturated vegetable fatty acids, in which lauric acid predominates. They are derived from purified and specially selected palm-seed oil, such as coconut and palm-kernel oil. The amount of lipid carrier depends on the solubility of the agent in the carrier or the amount needed for a suspension of the drug. This can range from 5 mg to 5 grams or more (for human or animal use).

Osmotic agents are incorporated into the core to provide the requisite osmotic driving force for release of the lipid carrier and active agent. The osmotic agent is preferably selected such that an osmotic pressure of 8 to 500 atmospheres can be generated, however osmotic pressures greater than zero are within guidelines. The amount of osmotic agent depends on its solubility in water and the total volume of the core. A sufficient amount of osmotic agent is required to ensure complete pumping of lipid carrier at a controlled rate. For complete pumping of lipid at a zero order rate the amount of osmotic agent required is that necessary to maintain a saturated solution of osmotic agent throughout the period of lipid pumping. Thus the ratio of the solubility to the density (s/p) is an indication of the efficiency of the osmotic agent. A lower s/p ratio indicates a more efficient osmotic agent. The general range of osmotic agent used is 20 to 80 percent of the tablet weight depending upon the choice of osmotic agent. Examples include magnesium sulfate, magnesium chloride, sodium chloride, lithium chloride, potassium sulfate, sodium carbonate, sodium sulfite, lithium sulfate, potassium chloride, calcium bicarbonate, sodium sulfate, calcium sulfate, potassium acid phosphate, calcium lactate, d-mannitol, urea, inositol, sorbitol, magnesium succinate, tartaric acid, carbohydrates such as fructose, sucrose, glucose, α-d-lactose monohydrate, and mixtures thereof. The osmotic agent(s) may be a water soluble active agent(s); however, a water insoluble active agent is still required. The compound is initially present in excess and it can be in any physical form such as particles, crystals, pellets, tablets, strips, films or granules. The osmotic pressure of saturated solutions of various osmotically effective compounds and for mixtures of compounds at 37° C. (body temperature), in water, is listed in Table I. In the table, the osmotic pressure is in atmospheres, atm. The osmotic pressure is measured in a commercially available osmometer that measures the vapor pressure difference between pure water and the solution to be analyzed, and according to standard thermodynamic principles, the vapor pressure ratio is converted into osmotic pressure difference. In Table I, osmotic pressures of from 20 atm to 500 atm are set forth; of course, the invention includes the use of lower osmotic pressures from greater than zero, and higher osmotic pressures than those set forth by way of example in Table I. For example, in the gastrointestinal tract, the osmotic pressure gradient across the wall in the compartment will be from greater than 0 up to 500 atm. That is, the osmotic pressure in the compartment will be typically in excess of 8 atm up to 500 atm.

TABLE I

| COMPOUND OR MIXTURE | OSMOTIC PRESSURE (atm) |
|---|---|
| Lactose-Fructose | 500 |

TABLE I-continued

| COMPOUND OR MIXTURE | OSMOTIC PRESSURE (atm) |
| --- | --- |
| Dextrose-Fructose | 450 |
| Sucrose-Fructose | 430 |
| Mannitol-Fructose | 415 |
| Sodium Chloride | 356 |
| Fructose | 335 |
| Lactose-Sucrose | 250 |
| Potassium Chloride | 245 |
| Lactose-Dextrose | 225 |
| Mannitol-Dextrose | 225 |
| Dextrose-Sucrose | 190 |
| Mannitol-Lactose | 170 |
| Sucrose | 150 |
| Mannitol-Lactose | 130 |
| Dextrose | 82 |
| Potassium Sulfate | 39 |
| Mannitol | 38 |
| Sodium Phosphate Tribasic.12H$_2$O | 36 |
| Sodium Phosphate Dibasic.7H$_2$O | 31 |
| Sodium Phosphate Dibasic.12H$_2$O | 31 |
| Sodium Phosphate Dibasic Anhydrous | 29 |
| Sodium Phosphate Monobasic.H$_2$O | 28 |

The specifications for the wall are summarized below and include:

| | | |
| --- | --- | --- |
| 1. | Wall thickness | 1 to 1000 preferably 50 to 300, microns |
| 2. | Wall wetability by lipid | Preferentially wetted by the lipid carrier over the aqueous solution of the osmotic agent, preferably better than cellulose acetate CA-320S |
| 3. | Water permeability | $1 \times 10^{-18}$ to $4 \times 10^{-15}$ cm$^3$ sec/g |
| 4. | Water Soluble Pore-forming additives | 0 to 150 parts, preferably 5 to 100 parts, per 100 parts wall polymer(s) |
| 5. | Plasticizer and flux regulating additives | 0 to 100, preferably 5 to 50 parts, per 100 parts wall polymer(s) |
| 6. | Release means | Preferably orifices, such as pores or holes 1 nm to 1 mm, preferably .01 to 200μ |

The water insoluble wall of the instant invention directly in contact with the core must be preferentially wetted by the active agent dissolved in the lipid carrier over the aqueous solution of osmotic agent so that active agent is pumped in preference to the osmotic agent.

A means must be provided for the active agent to be released through the water insoluble wall. This may be accomplished by holes in the wall, for example by the presence of pores and/or one or more direct holes.

A controlled porosity wall can be generically described as having a sponge-like appearance. The pores can be continuous pores that have an opening on both faces of a microporous lamina, pores interconnected through tortuous paths of regular and irregular shapes including curved, curved-linear, randomly oriented continuous pores, hindered connected pores and other porous paths discernible by microscopic examination. Generally, microporous lamina are defined by the pore size, the number of pores, the tortuosity of the microporous path and the porosity which relates to the size and number of pores. The pore size of a microporous lamina is easily ascertained by measuring the observed pore diameter at the surface of the material under the electron microscope. Generally, materials possessing from 5% to 95% pores and having a pore size of from 10 angstroms to 200 microns are preferred.

Any pore forming additives may be used in the instant invention. The microporous wall may be formed in situ, by a pore-former being removed by dissolving or leaching it to form the microporous wall during the operation of the system. The pores may also be formed in the wall prior to operation of the system by gas formation within curing polymer solutions which result in voids and pores in the final form of the wall. The pore-former can be a solid or a liquid. The term liquid, for this invention embraces semi-solids, and viscous fluids. The pore-formers can be inorganic or organic. The pore-formers suitable for the invention include pore-formers that can be extracted without any chemical change in the polymer. Solid additives include alkali metal salts such as sodium chloride, sodium bromide, potassium chloride, potassium sulfate, potassium phosphate, sodium benzoate, sodium acetate, sodium citrate, potassium nitrate and the like. The alkaline earth metal salts such as calcium chloride, calcium nitrate, and the like may also be used. The transition metal salts such as ferric chloride, ferrous sulfate, zinc sulfate, cupric chloride, and the like may also be used. Water may be used as the pore-former. The pore-formers include organic compounds such as organic acids and saccharides. The organic acids include tartaric acid, citric acid, and the like. The saccharides include the sugars, sucrose, glucose, fructose, mannose, galactose, aldohexose, altrose, talose, lactose, monosaccharides, disaccharides, and water soluble polysaccharides. Also, sorbitol, mannitol, organic aliphatic and aromatic polyols, including diols and polyols, as exemplified by polyhydric alcohols, poly(alkylene glycols), polyglycols, alkylene glycols, poly(α-ω)alkylenediols esters or alkylene glycols, poly vinylalcohol, poly vinyl pyrrolidone, and water soluble polymeric materials may be used. Pores may also be formed in the wall by the volatilization of components in a polymer solution or by chemical reactions in a polymer solution which evolves gases prior to application or during application of the solution to the core mass resulting in the creation of polymer foams serving as the porous wall of the invention. The pore-formers are nontoxic, and on their removal channels are formed that fill with fluid. The channels become a transport path for fluid. In a preferred embodiment, the non-toxic pore-forming agents are selected from the group consisting of inorganic and organic salts, carbohydrates, polyalkylene glycols, poly(α-ω) alkylenediols, esters of alkylene glycols, and glycols, that are used in a biological environment.

The microporous materials can be made by etched nuclear tracking, by cooling a solution of flowable polymer below the freezing point with subsequent evaporation of solvent to form pores, by gas formation in a polymer solution which upon curing results in pore formation, by cold or hot stretching at low or high temperatures until pores are formed, by leaching from a polymer a soluble component by an appropriate solvent, by ion exchange reaction, and by polyelectrolyte processes. Processes for preparing microporous materials are described in *Synthetic Polymer Membranes*, by R. E. Kesting, Chapters 4 and 5, 1971, published by McGraw Hill, Inc.; *Chemical Reviews*, Ultrafiltration, Vol. 18, pages 373 to 455, 1934; *Polymer Eng. and Sci.*, Vol. 11, No. 4, pages 284 to 288, 1971; *J. Appl. Poly. Sci.*, Vol. 15, pages 811 to 829, 1971; and in U.S. Pat. Nos.

3,565,259; 3,615,024; 3,751,536; 3,801,692; 3,852,224; and 3,849,528.

Any polymer permeable to water and lipid wettable may be used. Other polymers permeable to water but not well wetted by lipid may serve as exterior wall layers, in the event more than one wall layer is used. The permeability of the polymer with respect to the osmotic agent(s) generally should be less than 5% of its water permeability. Examples of water permeable, lipid wettable polymers as well as water permeable coatings for the outer wall layers include cellulose acetate and related cellulosic esters such as cellulose diacetate, cellulose triacetate, cellulose acetate propionate and cellulose acetate butyrate. Cellulose triacelylates such as cellulose trivalerate, cellulose trilaurate, cellulose tripalmitate, cellulose trisuccinate, cellulose triheptylate, cellulose tricaprylate, cellulose trioctanoate, and cellulose tripropionate may also be used. Cellulose diesters such as cellulose dicaprylate and cellulose dipentanate and esters prepared from acyl anhydrioles or acyl acids in an esterification reaction to yield esters containing different acyl groups attached to the same cellulose ploymer such s cellulose acetate valerate, cellulose acetate succinate, cellulose proprionate succinate, cellulose acetate octanoate, cellulose valerate palmitate, cellulose acetate palmitate and cellulose acetate heptanoate may also be used.

Additional polymers that can be used for the purpose of the invention include cellulose acetate acetoacetate, cellulose acetate chloroacetate, cellulose acetate furoate, dimethoxyethyl cellulose acetate, cellulose acetate carboxymethoxypropionate, cellulose acetate benzoate, cellulose butyrate naphtylate, cellulose acetate benzoate, methylcellulose acetate, methylcyanoethyl cellulose, cellulose acetate methoxyacetate, cellulose acetate ethoxyacetate, cellulose acetate dimethylsulfamate, ethylcellulose, ethylcellulose dimethylsulfamate, cellulose acetate p-toluene sulfonate, cellulose acetate methylsulfonate, cellulose acetate dipropylsulfamate, cellulose acetate butylsulfonate, cellulose acetate laurate, cellulose stearate, cellulose acetate methylcarbamate, agar acetate, amylose triacetate beta glucan acetate, beta glucan triacetate, acetaldehyde dimethyl acetate, cellulose acetate ethyl carbamate, cellulose acetate phthalate, cellulose acetate dimethyl aminoacetate, cellulose acetate ethyl carbonate, poly (vinyl methyl) ether copolymers, cellulose acetate with acetylated hydroxyethy cellulose, hydroxylated ethylenevinylacetate, poly (ortho ester)s, polyacetals, semipermeable polyglycolic or polylactic acid and derivatives thereof, selectively permeable associated polyelectrolytes, polymers of acrylic and methacrylic acid and esters thereof, film forming materials with a water sorption of one to fifty percent by weight at ambient temperatures with a presently preferred water sorption of less than thirty percent, acylated polysaccharides, acylated starches, aromatic nitrogen containing polymeric materials that exhibit permeability to aqueous fluids, membranes made from polymeric epoxides, copolymers of alkylene oxides and alkyl glycidyl ethers, polyurethanes, and the like. Admixtures of various polymers may also be used.

The polymers described are known to the art or they can be prepared according to the procedures in *Encyclopedia of Polymer Science and Technology*, Vo. 3, pages 325 to 354, and 459 to 549, published by Interscience Publishers, Inc., New York, in *Handbook of Common Polymers* by Scott, J. R. and Roff, W. J., 1971 published by CRC Press, Cleveland, Ohio; and in U.S. Pat. Nos. 3,133,132; 3,173,876; 3,276,586; 3,541,055; 3,541,006; and 3,564,142.

It is generally desirable from a preparation standpoint to disolve the polymer in a solvent. Exemplary solvents suitable for manufacturing the wall of the osmotic device include inert inorganic and organic solvents that do not adversely harm the core, wall, and the materials forming the final wall. The solvents broadly include members selected from the group consisting of aqueous solvents, alcohols, ketones, esters, ethers, aliphatic hydrocarbons, halogenated solvents, cycloaliphatic, aromatics, heterocyclic solvents and mixtures thereof. Typical solvents include acetone, diacetone alcohol, methanol, ethanol, isopropyl alcohol, butyl alcohol, methyl acetate, ethyl acetate, isopropyl acetate, n-butyl acetate, methyl isobutyl ketone, methyl propyl ketone, n-hexane, ethyl lactate, n-heptane, ethylene glycol monoethyl ether, ethylene glycol monoethyl acetate, methylene dichloride, ethylene dichloride, propylene dichloride, carbon tetrachloride, nitroethane, nitropropane, tetrachloroethane, ethyl ether, isopropyl ether, cyclohexane, cyclooctane, dimethylbromamide, benzene, toluene, naphtha, 1,4-dioxane, tetrahydrofuran, diglyme, water, and mixtures thereof such as acetone and water, acetone and methanol, acetone and ethyl alcohol, methylene dichloride and methanol, and ethylene dichloride and methanol. Illustrative of mixed solvents are acetone-methanol (80:20), acetone-ethanol (90:10), methylene dichloride-methanol (80:20), nitroethane-ethanol (50:50), nitroethane-ethanol (80:20), ethyl acetate-ethanol (80:20), ethylene dichloride-methanol (80:20), methylenedichloride-methanol (78:22), acetone-water (90:10), chloroform-ethanol (80:20), methylenedichloride-ethanol (79:21), methylene chloride-methanol-water (75:22:3), carbontetrachloride-methanol (70:30), expressed as (weight:weight), and the like.

Exemplary plasticizers suitable for the present purpose include plasticizers that lower the temperature of the second-order phase transition of the wall or the elastic modulus thereof; and also increase the workability of the wall, its flexibility and its permeability to water. Plasticizers operable for the present purpose include both cyclic and acyclic plasticizers. Typical plasticizers are those selected from the group consisting of phthalates, phosphates, citrates, adipates, tartrates, sebacates, succinates, glycolates, glycerolates, benzoates, myristates, sulfonamides and halogenated phenyls. Generally, from 0 to 100 parts of a plasticizer or a mixture of plasticizers are incorporated into 100 parts of wall polymer(s).

Specific exemplary plasticizers include dialkyl phthalates, dicycloalkyl phthalates, diaryl phthalates and mixed alkylaryl phthalates such as diethyl phthalate, dipropyl phthalate, di-(2-ethyl-hexyl)-phthalate, di-isopropyl phthalate, diamyl phthalate and dicapryl phthalate; alkyl and aryl phosphates such as tributyl phosphate, tri-(2-ethyl-hexyl)trimellitate, trioctyl phosphate, tricresyl phosphate and trioctyl phosphate, tricresyl phosphate and triphenyl phosphate; alkyl citrate and citrate esters such as tributyl citrate, triethyl citrate, and acetyl triethyl citrate; alkyl adipates such as dioctyl adipate, diethyl adipate and di-(2-methoxyethyl)-adipate; dialkyl tartrates such as diethyl tartrate and dibutyl tartrate; alkyl sebacates such as diethyl sebacate, dipropyl sebacate and dinonyl sebacate; alkyl succinates such as diethyl succinate and dibutyl succinate; alkyl glycolates, alkyl glycerolates, glycol esters and glycerol esters such as glycerol diacetate, glycerol triacetate, glycerol monolactate diacetate, methyl phthalyl ethyl glycolate, butyl phthalyl butyl glycolate, ethylene glycol diacetate, ethylene glycol dibutyrate, triethylene glycol diacetate, triethylene glycol dibutyrate and triethylene glycol dipropionate. Other plasticizers include camphor, N-ethyl-(o- and p-toluene) sulfonamide, benzophenone, N-cyclohexyl-p-toluene sulfonamide.

Suitable plasticizers can be selected for blending with the wall forming materials by selecting plasticizers that have a high degree of solvent power for the materials, that are compatible with the materials over both the processing and use temperature range, that exhibit permanence as seen by their strong tendency to remain in the plasticized wall, that impart flexibility to the material and that are non-toxic to animals, humans, avians, fishes and reptiles. Procedures for selecting a plasticizer having the described characteristics are disclosed in the *Encyclopedia of Polymer Science and Technology*, Vol. 10, pages 228 to 306, 1969, published by John Wiley & Sons, Inc. Also, a detailed description pertaining to the measurement of plasticizer properties including solvent parameters and compatibility such as the Hildebrand solubility parameter, $\delta$, the Flory-Huggins interaction parameter, $\chi$, and the cohesive-energy density, CED, parameters are disclosed in *Plasticization and Plasticizer Processes*, Advances in Chemistry Series 48, Chapter 1, pages 1 to 26, 1965, published by the American Chemical Society. The amount of plasticizer added generally is an amount sufficient to produce the desired wall properties and it will vary according to the plasticizer and the wall materials. Usually about 0 to 100 parts, preferably 5 to 50 parts, of the plasticizer can be used for 100 parts of wall polymer(s).

The expressions "flux regulating additives", "flux enhancing agent" and "flux decreasing agent" as used herein mean a compound that when added to a wall forming material assists in regulating the fluid permeability into the core. The agent can be preselected to increase or decrease the fluid flux. Agents that produce a marked increase in permeability to fluid such as water, are often essentially hydrophilic, while those that produce a marked decrease to fluids such as water, are essentially hydrophobic. The flux regulators in some embodiments also can increase the flexibility and porosity of the lamina. Examples of flux regulators include polyhydric alcohols and derivatives thereof, such as polyalkylene glycols of the formula H—(O-alkylene)-$_n$—OH wherein the bivalent alkylene radical is straight or branched chain and has from 1 to 10 carbon atoms and n is 1 to 500 or higher. Typical glycols include polyethylene glycols 300, 400, 600, 1500, 1540, 4000, 6000, and 20,000 of the formula H—(OCH$_2$CH$_2$)$_n$—OH wherein n is respectively 5 to 500. Other polyglycols include the low molecular weight glycols such as polypropylene, polybutylene and polyamylene.

Additional flux regulators include poly ($\alpha,\omega$) alkylenediols wherein the alkylene is straight or branched chain of from 2 to 10 carbon atoms such as poly(1,3)-propanediol, poly(1,4)butanediol, poly(1,5)pentanediol and poly(1,6)hexanediol. The diols also include aliphatic diols of the formula HOC$_n$H$_{2n}$OH wherein n is from 2 to 10 and diols are optionally bonded to a non-terminal carbon atom such as 1,3-butylene glycol, 1,4-pentamethylene glycol, 1,5-hexamethylene glycol and 1,8-decamethylene glycol; and alkylenetriols having 3 to 6 carbon atoms such as glycerine, 1,2,3-butanetriol, 1,2,3-pentanetriol, 1,2,4-hexanetriol and 1,3,6-hexanetriol.

Other flux regulators include esters and polyesters of alkylene glycols of the formula HO—(alkylene-O)$_n$—H wherein the divalent alkylene radical includes the straight chain groups and the isomeric forms thereof having from 2 to 6 carbons and n is 1 to 14. The esters and polyesters are formed by reacting the glycol with either a monobasic or dibasic acid. Exemplary flux regulators are ethylene glycol dipropionate, ethylene glycol butyrate, ethylene glycol diacetate, triethylene glycol diacetate, butylene glycol dipropionate, polyester of ethylene glycol with succinic acid, polyester of diethylene glycol with maleic acid, and polyester of triethylene glycol with adipic acid.

The amount of flux regulator added to a material generally is an amount sufficient to produce the desired wall permeability, and it will vary according to the lamina forming material and the flux regulator used to modulate the permeability. Usually from 0 parts up to 150 parts, or higher of flux regulator, per 100 parts of wall polymer(s), can be used to achieve the desired results.

The critical feature of the instant invention relates to the wetting of the wall preferentially by the lipid carrier over that of a saturated solution of the osmotic agent. A study has been done to demonstrate this preferential wettability using a series of cellulose acetate films. The films were prepared on glass by evaporation of the solvent from a solution of the polymer. A section of clear smooth film was used to measure the contact angle made by either a lipid drop or saturated sodium chloride drop. The films were first equilibrated in either the lipid carrier (Witepsol ® H-35) or saturated sodium chloride solution.

A section of the polymer was then dried using a piece of paper toweling and attached to a glass slide by double stick adhesive tape. The slide was immersed in the lipid if equilibrated in saturated sodium chloride or in saturated sodium chloride when equilibrated with lipid (Witepsol ® H-35). Drops of lipid (Witepsol ® H-35) of less than 2 $\mu$l were allowed to rise through the saturated sodium chloride solution and contact the polymer surface. Likewise drops of saturated sodium chloride were allowed to sink to the surface of the polymer through the lipid. Measurements were made at 37° C. using a microscope fitted with a micrometer eyepiece which could measure the drop width and height or the contact angle directly; both procedures gave similar results. The following table presents the results of this study.

TABLE II

| Wettability of Various Cellulosic Films | | |
|---|---|---|
| | Contact Angle | |
| Polymer[a] Film | Saturated Sodium Chloride Drop | Lipid Drop (Witepsol ® H-35) |
| Cellulose Acetate Propionate CAP-436-20 | 150 | 51.5 |
| Cellulose Acetate Butyrate CAB-553-0.4 | 146 | 54.5 |
| Cellulose Acetate CA-436-80S | 121 | 82.2 |
| Cellulose Acetate CA-398-10 | 115 | 96.4 |
| Cellulose Acetate | 91 | 113 |

TABLE II-continued

| | Wettability of Various Cellulosic Films | |
|---|---|---|
| | Contact Angle | |
| Polymer[a] Film | Saturated Sodium Chloride Drop | Lipid Drop (Witepsol ® H-35) |
| CA-320S | | |

[a]Cellulose Acetates obtained from Eastman Chemical Co., Kingsport, Tenn.

A smaller contact angle indicates greater wetting of the polymer by the liquid drop.

Table II is arranged in order of decreasing lipid wettability. In fact, Cellulose acetate CA-320S is not preferentially wetted by the lipid; however, cellulose acetate CA-398-10 and polymers listed above it are preferentially wetted by the lipid. The requirement of preferential wetting of the inner wall polymer by the lipid over that of a saturated solution of the osmotic agent is the critical feature of the instant invention and has been demonstrated experimentally. The result of Example 5 in which CA 320-S was used as the wall polymer showed that preferential pumping of the lipid does not occur in this case; whereas, the result of example 2 in which CA 398-10 was used as the wall polymer showed that preferential pumping of the lipid does occur.

Referring to FIGS. 1–5, the lipid osmotic pump is typically in the form of a single coated tablet. FIGS. 1-5 have the features and elements as described below.

FIG. 1 illustrates a typical tablet in which the core is a solid at room temperature and consists of active agent(s) dissolved or suspended in the lipid carrier (10) and osmotic agent(s) (11) surrounded by the water insoluble wall (12) which may be applied to the core by spray coating procedures. The wall is comprised of a polymeric material that is insoluble in the fluids of the environment of intended use (usually water) and which has mechanically produced holes (13) for pumping out of the tablet contents.

Figure 2:
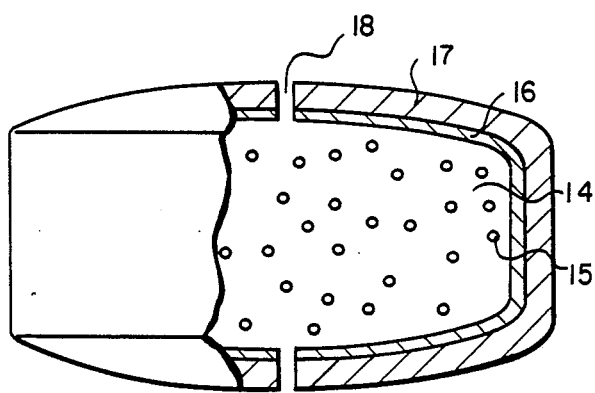
FIG. 2 is a cutaway of a lipid osmotic pump with a wall that consists of two different polymeric materials.

FIG. 2 illustrates a typical lipid osmotic tablet which has a solid core at room temperature and consists of active agent(s) dissolved or suspended in the lipid carrier (14) and osmotic agent(s) (15) surrounded by the water insoluble wall which consist of two different polymeric materials. A very lipid wettable wall (16) is in direct contact with the core while a somewhat less lipid wettable layer (17) provides the outer wall. Holes (18) for pumping of the tablet contents are produced in both the wall layers.

Figure 3:
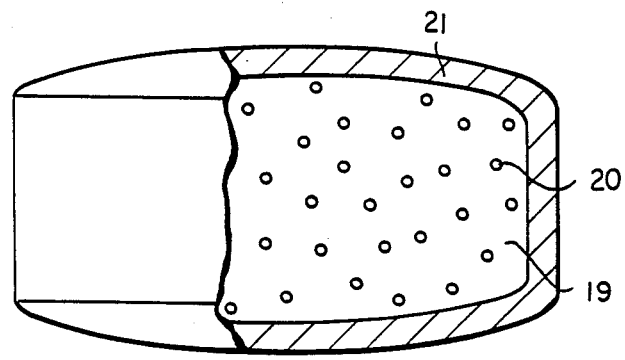
FIG. 3 is a cutaway of a lipid osmotic pump having a water insoluble wall which has added pore formers that will dissolve in the environmental fluids of use.

FIG. 3 illustrates a lipid osmotic pump which has a solid core at room temperature and consists of active agent(s) dissolved in the lipid carrier (19) and osmotic agent(s) (20) surrounded by the water insoluble wall (21) which in this case has added pore formers that will dissolve in the environmental fluids of use.

Figure 4:
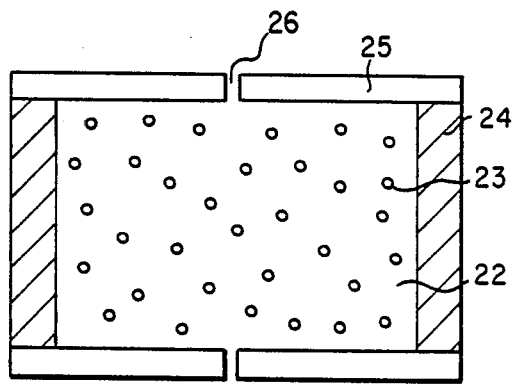
FIG. 4 is a lipid osmotic device wherein the wall is a rigid insoluble cylinder having polymeric films glued to the ends and having a hole through each film.

FIG. 4 illustrates a lipid osmotic device which can be prepared with either a solid or liquid core at room temperature and consists of active agent(s) dissolved or suspended in the lipid carrier (22) and osmotic agent(s) (23) surrounded by a rigid insoluble cylinder (24) to which the polymeric films (25) have been glued. Holes (26) have been produced in the films to allow for pumping of the contents, however, pore forming additives could also be incorporated in the polymer films.

Figure 5A:
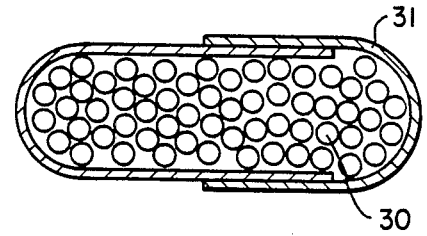
FIG. 5 is a cutaway and cross-section of a hard gelatin capsule filled with lipid osmotic pump pellets.
Figure 5B:
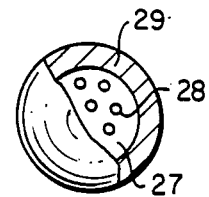

FIG. 5 illustrates a lipid osmotic pellet which has a solid core at room temperature and consist of active agent(s) dissolved in the lipid carrier (27) and osmotic agent(s) (28) surrounded by the water insoluble wall (29) which has added pore-formers that will dissolve in the environmental fluids of use and leach out of the wall creating pores from which the contents can be pumped. Also shown in FIG. 5 is a hard gelatin capsule (31) filled with the pellets (30) which illustrates one method of administering this type of dosage form.

Figure 6:
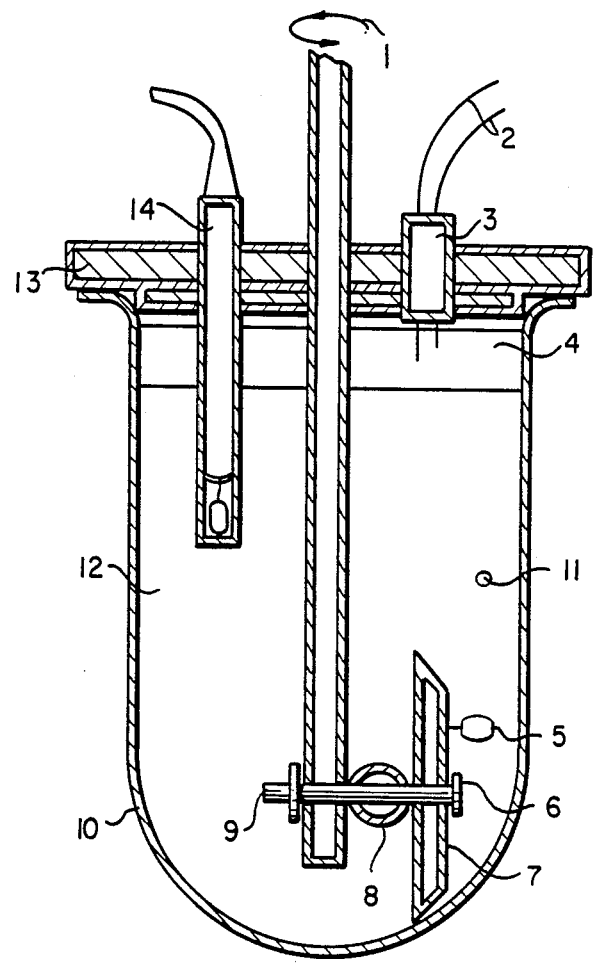
FIG. 6 is the device used in the Examples using tablets to measure the release of drug and/or lipid carrier from the lipid osmotic tablets.

FIG. 6 shows the device used in the Examples to measure the release of drug and/or lipid carrier from the lipid osmotic tablets and devices. Standard U.S.P. dissolution flask (10) is used; however, the standard paddle has been replaced by a rod (1) which is rotated at about 8 rpm. On the end of the shaft is a rubber wheel (7) attached to the shaft by means of an axle (6), spacer (8) and nut (9). The tablet(s) (5) is held on the rubber wheel (7) by a spring clamp such that as the shaft rotates the wheel rides on the flask and rotates which in turn inverts the tablet approximately 10 revolutions per minute. In operation the flsk is filled with (900 ml) water or other dissolution media (12) and a layer of isopropylmyristate (4) (100 ml) serves to collect and dissolve the lipid carrier drops (11) which rise from the tablet. A plexiglass lid (13) is fitted with a holder (3) to which the tubes (2) are inserted, so that they are held within the IPM layer. The IPM is pumped continuously through a flow cell within a spectrophotometer (not shown). The plexiglass lid (13) also holds a conductance cell in place.

EXAMPLE 1

Lipid osmotic pumps are generally configured as tablet-shaped dosage forms, as shown in FIGS. 1–3. In this and following examples, tablet is used to refer to the general shape and appearance of these lipid osmotic pumps. Tablets for the osmotically controlled release of the beneficial drug timolol were made as follows: First 60 g of commercially available Witepsol ® H-35 suppository base (lipid carrier) and 40 g (40 to 60 mesh) reagent grade sodium chloride (osmotic agent) and 2 g of timolol anhydrous free base (active agent) and 0.14 g of scarlet red (lipid soluble dye) were melted together. Upon melting, the timolol and scarlet red dye dissolved in the lipid carrier and the sodium chloride was suspended by rapid mixing. This material was poured into a container of liquid nitrogen causing rapid solidification. The larger chunks of material were broken up and made into granules by forcing the material through standard screens which had been precooled with liquid nitrogen or dry ice. The material was passed through a progression of screens of decreasing size (increasing screen number) to a final mesh of 20–25. The screening work was performed in a dry room of 10 to 30% relative humidity to reduce the amount of water condensation on the granules. Solid tablet cores were prepared by taking approximately 400 mg of the granules and compressing them on a Crver ® press using cold ⅜ inch ball-shaped punches to a pressure of 1 to 2 tons. After sitting for a day or more to increase their hardness the tablets were coated in a model HCT-Mini Hi-coater ® (Freund). Approximately 500 cc of 5/16 inch extra deep concave filler tablets prepared from Avicel ® PH101, (microcrystalline cellulose, manufactured by FMC Corporation), lactose, cornstarch and magnesium stearate were used to fill the coating pan and to set the coating conditions of inlet air temperature, outlet air temperature and spray rate before the lipid tablet cores were added and coated. The coating solutions were as follows: coating Solution A contained 700 ml dichloromethane (solvent), 300 ml absolute methanol (solvent), 5 g cellulose acetate butyrate (Eastman CAB-553-0.4) and 1.25 g of polyethylene glycol 400 (plasticizer and flux enhancing agent). Solution B contained 700 ml dichloromethane, 300 ml absolute methanol, 20 g cellulose acetate (Eastman CA-398-10), and 5 g of polyethylene glycol 400. Coating conditions were set up as follows: pan rotation 24 rpm, atomizing air flow 1 Kg/cm$^2$, coating solution flow rate 10 ml/min, and inlet air temperature (43° C.) adjusted to give an air outlet temperature of 28°-29° C. After conditions were stabilized the lipid tablet cores were added and coated for 29 minutes with Solution A followed by 70 minutes with Solution B. The total polymer coat thickness was about 90 $\mu$. The coated tablets (see FIG. 2) were allowed to dry at room temperature exposed to the atmosphere. Two holes, one in each face, were made using a 100$\mu$ diameter needle.

The in vitro performance of the tablets in water was measured using the setup shown in FIG. 6. The release of the lipid carrier containing timolol and scarlet red from the tablet took place through the holes in each face. Droplets of lipid broke from the surface of the tablet and rose to the isopropyl myristate (IPM) layer (cf FIG. 6) where they dissolved releasing timolol and scarlet red. The rate of release of lipid carrier was monitored by following the absorption of scarlet red in the IPM layer with time. Release of the aqueous sodium chloride solution was followed by measuring the conductance of the aqueous solution.

Figure 7:
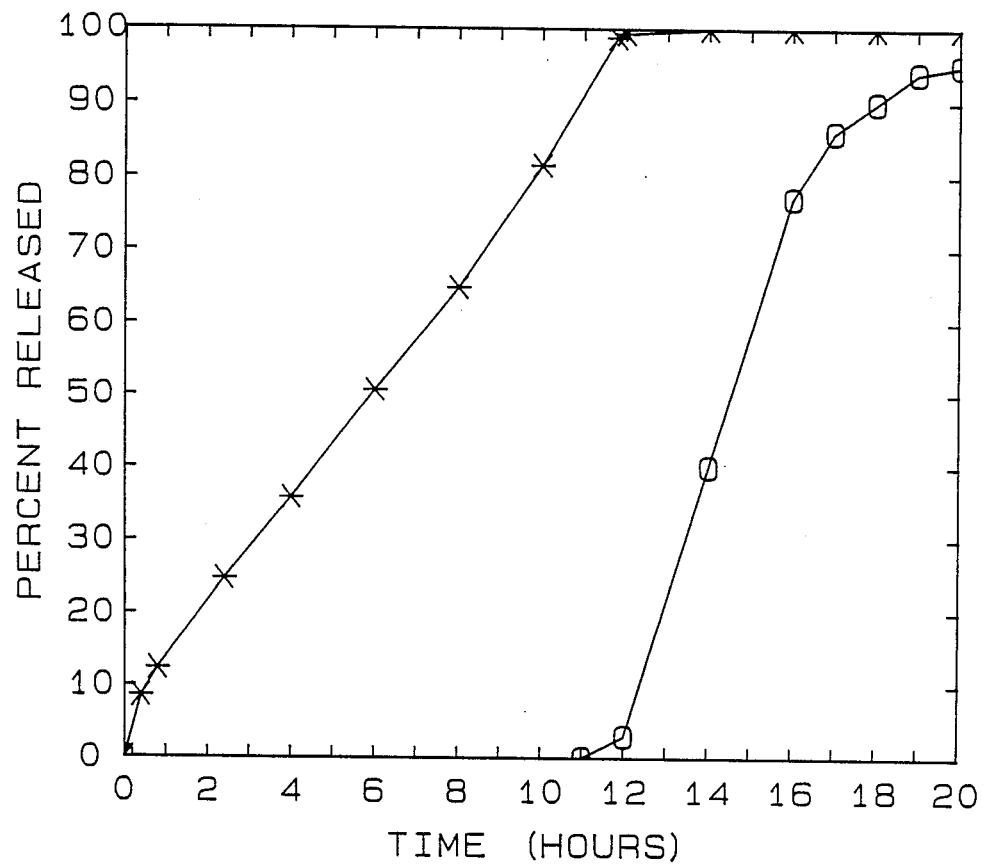
FIG. 7 is the release profile (percent released versus time) of lipid carrier/active agent and osmotic agent from the tablet used in Example 1.

FIG. 7 shows the release profile of the scarlet red (*) (lipid carrier and active agent) from the tablet as well as the osmotic agent, sodium chloride (O). The critical features of the system observed are: First, the lipid carrier including the active agent (Witepsol ® and timolol) are pumped at a nearly constant rate (zero order) from the tablet. Second, following lipid release the salt solution is pumped from the tablet demonstrating the preferential pumping of the lipid carrier over the aqueous solution which is a key feature of the system.

The apparent permeability of the coating on these lipid osmotic pumps can be calculated from the following equation.

$$\text{apparent permeability} = \frac{dv}{dt} \cdot \frac{h}{A} \cdot \frac{1}{\pi}$$

where dv/dt is the volume of lipid pumped per second, h is the coating thickness, A is the surface area of the tablet and $\pi$ is the osmotic pressure. All units are expressed in grams, centimeters and seconds.

The approximate apparent parmeability of the tablet coatings of Example 1 is $3.6 \times 10^{-16}$ cm$^3$ sec/g where
dv/dt = $3.5 \times 10^{-6}$ cm$^3$/sec p1 A = 2.5 cm$^2$
h = 0.009 cm
$\pi = 3.6 \times 10^8$ g/cm-sec$^2$

EXAMPLE 2

Figure 8:
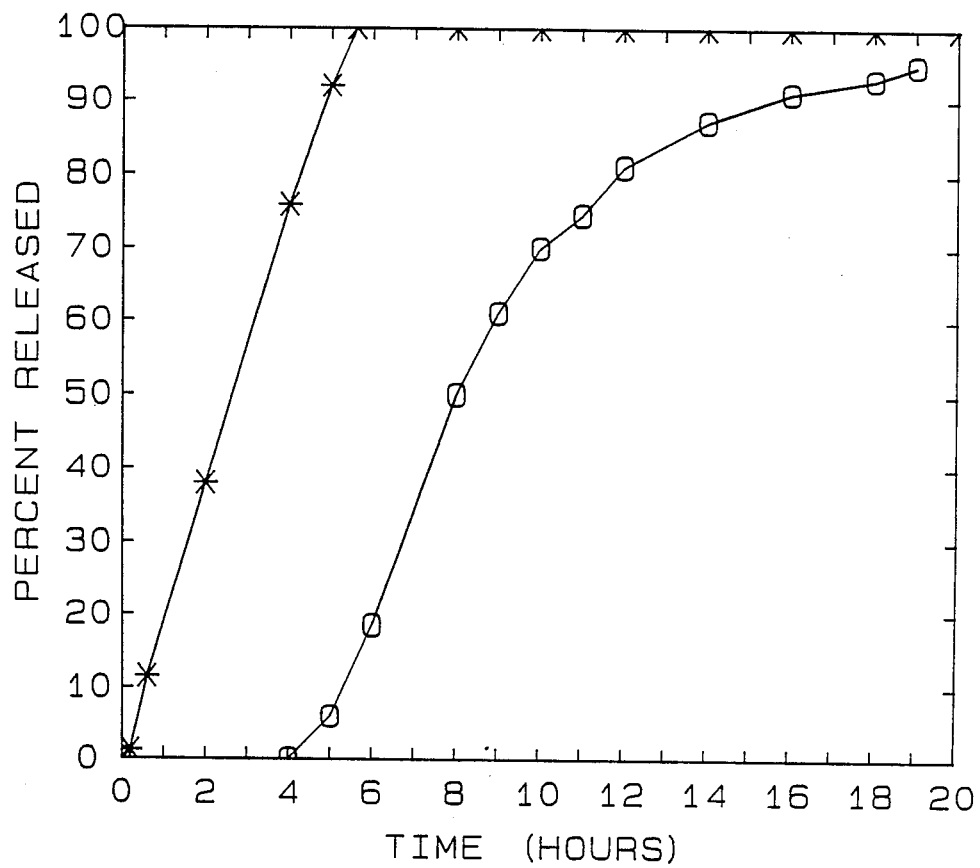
FIG. 8 is the release profile of the tablet used in Example 2.

Tablets (see FIG. 1) were prepared according to the procedure of Example 1, wherein the conditions were as described except that coating Solution A was not applied; only Solution B was used. Coating thickness was about 70$\mu$. The release profile of these tablets is shown in FIG. 8 where scarlet red release (*) (lipid carrier and timolol) and the osmotic agent sodium chloride (O) are shown. The release rate is faster than in Example 1 because of the lack of the cellulose acetate butyrate coat which is less permeable to water than cellulose acetate and the polymer coat is not as thick.

EXAMPLE 3

Figure 9:
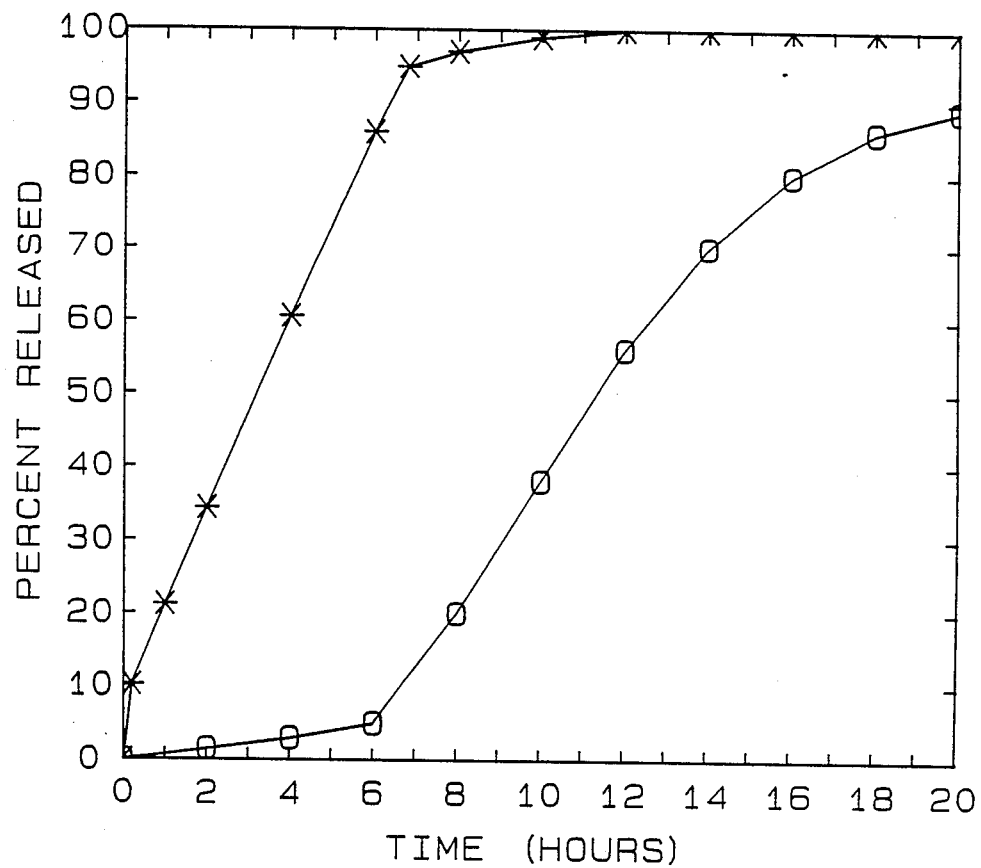
FIG. 9 is the release profile of the tablet used in Example 3.

Tablets (see FIG. 2) were prepared according to the procedure of Example 1, wherein the conditions were as described except that coating Solution A contained 700 ml dichloromethane, 300 ml absolute methanol, 20 g cellulose acetate (Eastman CA-436-80S) and 8 g of polyethylene glycol 400 and coating Solution B contained 700 ml of dichloromethane, 300 ml absolute methanol, 20 g cellulose acetate (Eastman CA-398-10), and 8 g of polyethylene glycol 400. Seven hundred ml of Solution A were applied at 10 ml/min followed by 1000 ml of Solution B applied at 8 ml/min. Total thickness of the coats was about 150$\mu$. The release profiles of scarlet red (*) (lipid and active agent) and sodium chloride (o) (osmotic agent) are shown in FIG. 9.

EXAMPLE 4

Figure 10:
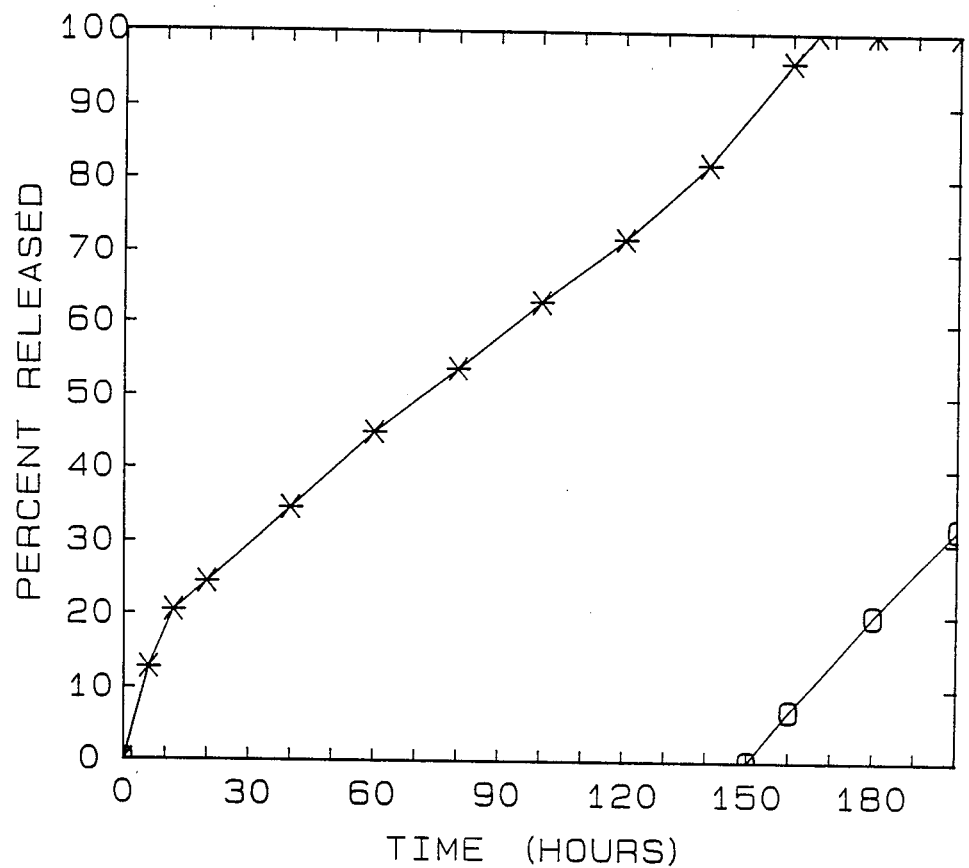
FIG. 10 is the release profile of the tablet used in Example 4.

Tablets (see FIG. 1) were prepared according to the procedure of Example 1 wherein the conditions were as described except that coating Solution A contained 750 ml of methylene chloride, 250 ml of anhydrous methanol, 20 g of cellulose acetate propionate (Eastman CAP-482-20) and 5 g of polyethylene glycol 400. Tablets were coated at a rate of 8 ml/min for 1 hour as the only coating material which was about 70$\mu$ thick. FIG. 10 shows the release profiles of the scarlet red (*) (lipid carrier plus drug) and the sodium chloride (o) (osmotic agent). The release rate was very slow due to the lower permeability of the coating material.

EXAMPLE 5

Figure 11:
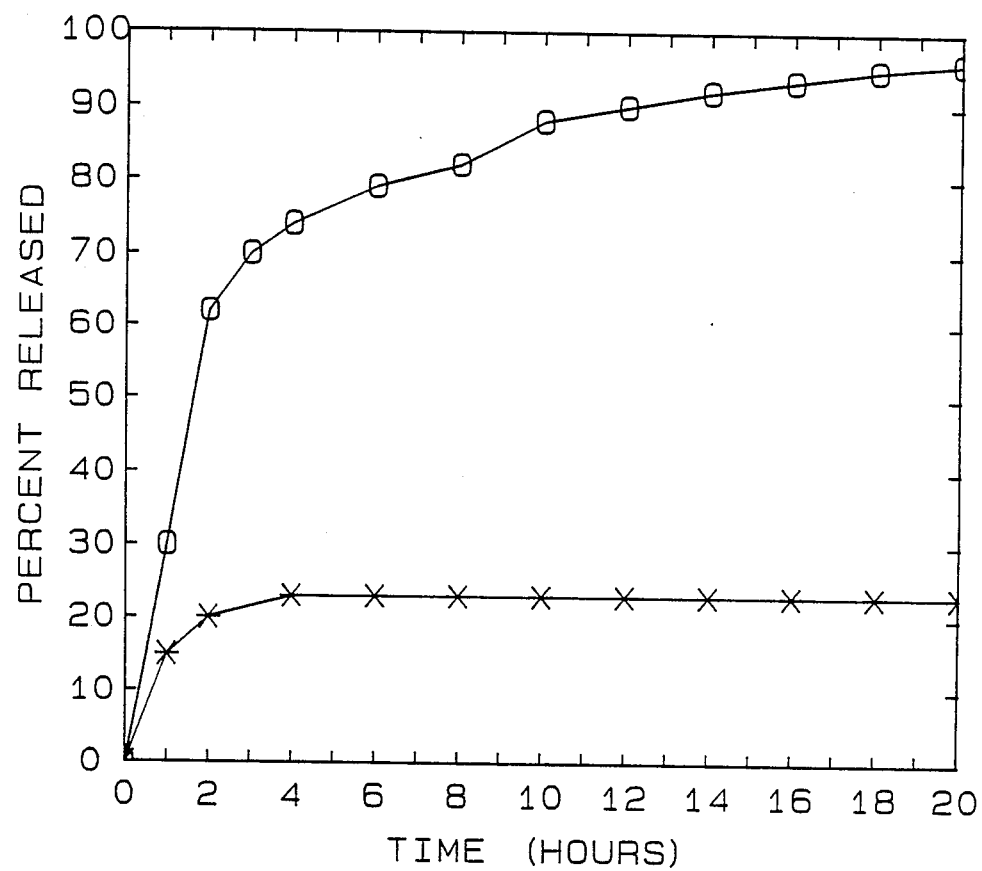
FIG. 11 is the release profile of the tablet used in Example 5.

Tablets (see FIG. 1) were prepared according to the procedure of Example 1, wherein the conditions were as described except that coating Solution A contained 750 ml of dichloromethane, 250 ml anhydrous methanol, 20 g of cellulose acetate (Eastman CA-320-S) and 5 g polyethylene glycol 400. The coating solution was applied at a rate of 6.5 ml/min for 20 minutes then at 8 ml/min for 150 minutes. This was the only coat applied to these tablets which was about 115$\mu$ thick. FIG. 11 shows the release profiles of the scarlet red (*) (lipid carrier and timolol) and the sodium chloride (o) (osmotic agent). The results show that a coating as hydrophilic as cellulose acetate (Eastman CA-320-S) is not sufficiently wetted by the lipid carrier to allow the system to perform properly, that is, to pump lipid preferentially over that of the aqueous solution. Thus, cellulose acetate coating materials must exhibit better lipid wetting than cellulose acetate (Eastman CA-320-S) such as the coatings described in Examples 1-4.

EXAMPLE 6

Figure 12:
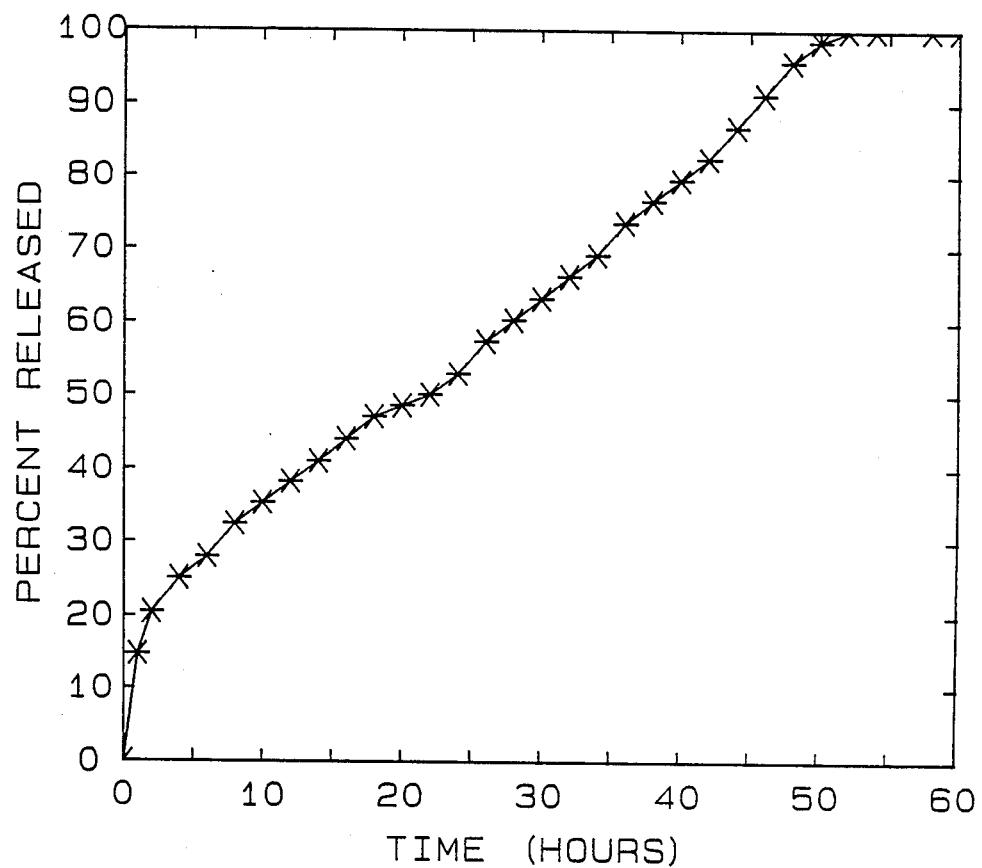
FIG. 12 is the release profile of the tablet used in Example 6.

Tablets (see FIG. 1) were prepared according to the procedure of Example 1 wherein the conditions were as described except that coating Solution A contained 700 ml dichloromethane, 300 ml absolute methanol, 20 g cellulose acetate butyrate (Eastman CAB-5534-0.4) and 5 g of polyethylene glycol 400. This coating solution was applied at a rate of 8 ml/min for 30 minutes as the only coat which was about 70$\mu$ thick. Also, the release rate of timolol (*) was followed at its absorbance maximum of 294 nm in the aqueous phase which was 900 ml of pH 1 hydrochloric acid solution. The release of timolol is shown in FIG. 12. The release of sodium chloride was not followed, however salt crystals were present within the unit at the point where essentially all the lipid had been pumped from the tablet.

EXAMPLE 7

Figure 13:
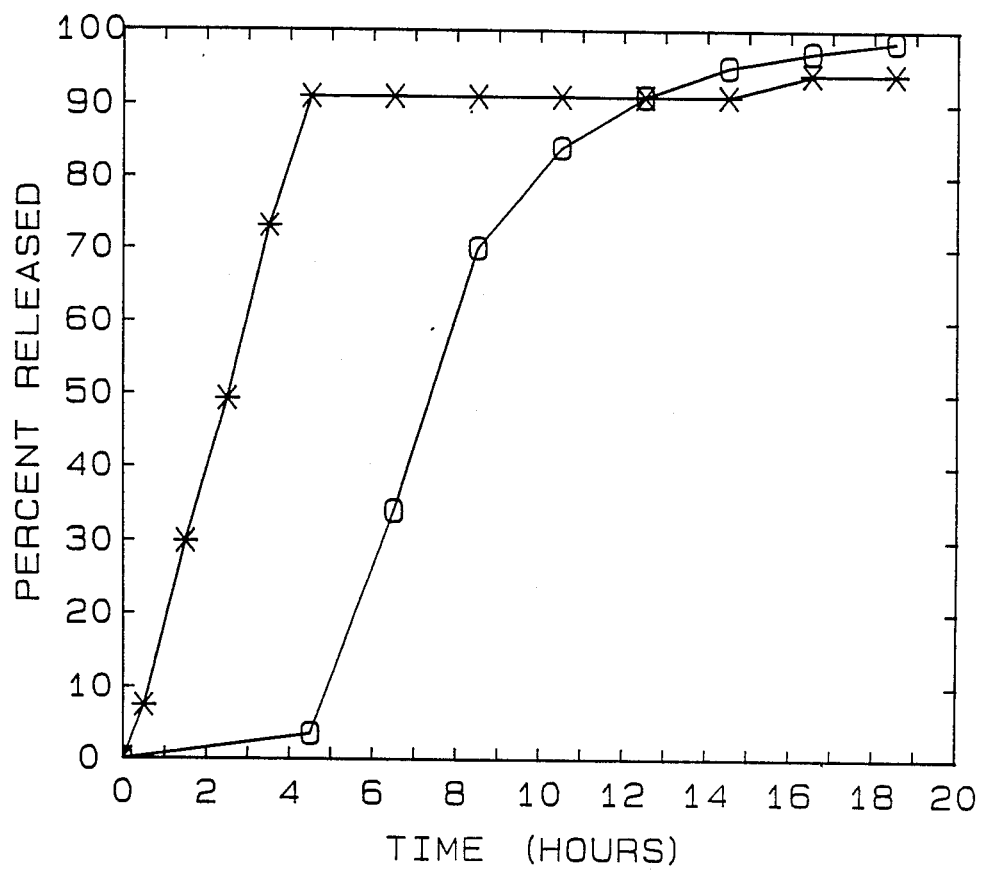
FIG. 13 is the release profile of the tablet used in Example 7.

Tablets (see FIG. 2) were prepared according to the procedure of Example 1, wherein the conditions were as described except that 40 g of potassium chloride (osmotic and active agents) was used in place of the sodium chloride. Also the two coating solutions contained: Solution C, 750 ml of dichloromethane, 250 ml of anhydrous methanol, 20 g of cellulose acetate (Eastman CA-436-80S) and 8 g of polyethylene glycol 400; and Solution D, 750 ml of dichloromethane, 250 ml of anhydrous methanol, 20 g of cellulose acetate (Eastman CA-398-10) and 8 g of polyethylene glycol 400. Solution C was coated at 10 ml/min for 75 minutes and solution D at 8 ml/min. for 120 minutes for a total coating thickness of about 185μ. The release rates of scarlet red (*) (lipid carrier and timolol) and potassium chloride (o) (osmotic agent and drug) are shown in FIG. 13. Two different drugs with two different release rates, in this case timolol and potassium chloride, may thus be used.

EXAMPLE 8

Figure 14:
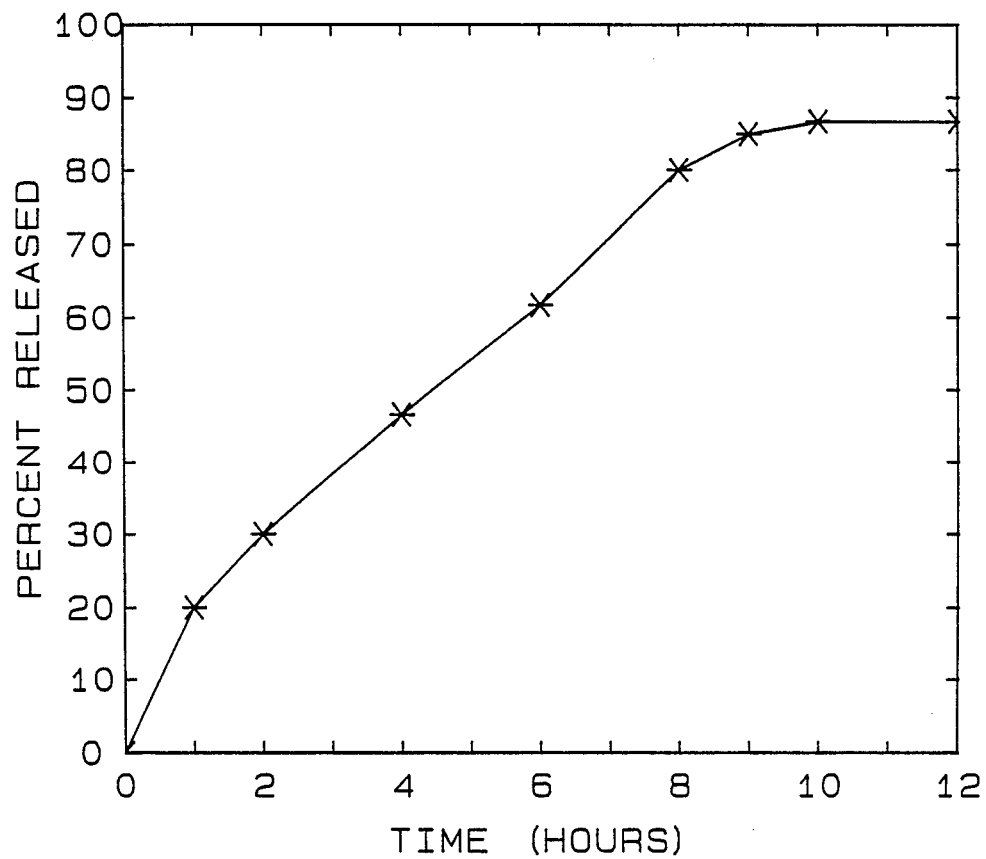
FIG. 14 is the release profile of the tablet used in Example 8.

Tablets (see FIG. 2) were prepared according to the procedure of Example 1, wherein the conditions were as described except that 40 g of Witepsol H-35, 7.2 g of mannitol, 2 g of timolol and 0.14 g of scarlet red were used in the core material. In addition, 10 mannitol pellets approximately 16 mg each (⅛"×1/16" standard concave tablets) and 207 mg of the lipid granules were weighed and sufficient mannitol (25–40 mesh) was added to give a final weight of 420 mg. The mixture was then tableted as described in Example 1. Also the coating procedure was the same as described in Example 7. The release rates of scarlet red (*) (lipid carrier and timolol) are shown in FIG. 14.

EXAMPLE 9

Tablets (see FIG. 2) were prepared according to the procedure of Example 1, wherein the conditions were as described except that 55 g Witepsol ® H-35, 40 g sodium chloride, 2 g of indomethacin acid (less than 50 microns particle size) and 0.14 g scarlet red made up the core material. Most of the indomethacin did not dissolve in the lipid carrier, and was present as a suspension of fine particles. Also coating Solutions C and D were as described in Example 7 where C was applied at a rate of 5.1 ml/min for 60 minutes then 7.6 ml/min for 30 minutes, and 10 ml/min for 15 minutes. Solution D was applied at 10 ml/min for 45 minutes and 7.6 ml/min for 45 minutes for a total thickness of about 150μ. Also 500μ holes were drilled into each tablet face.

Figure 15:
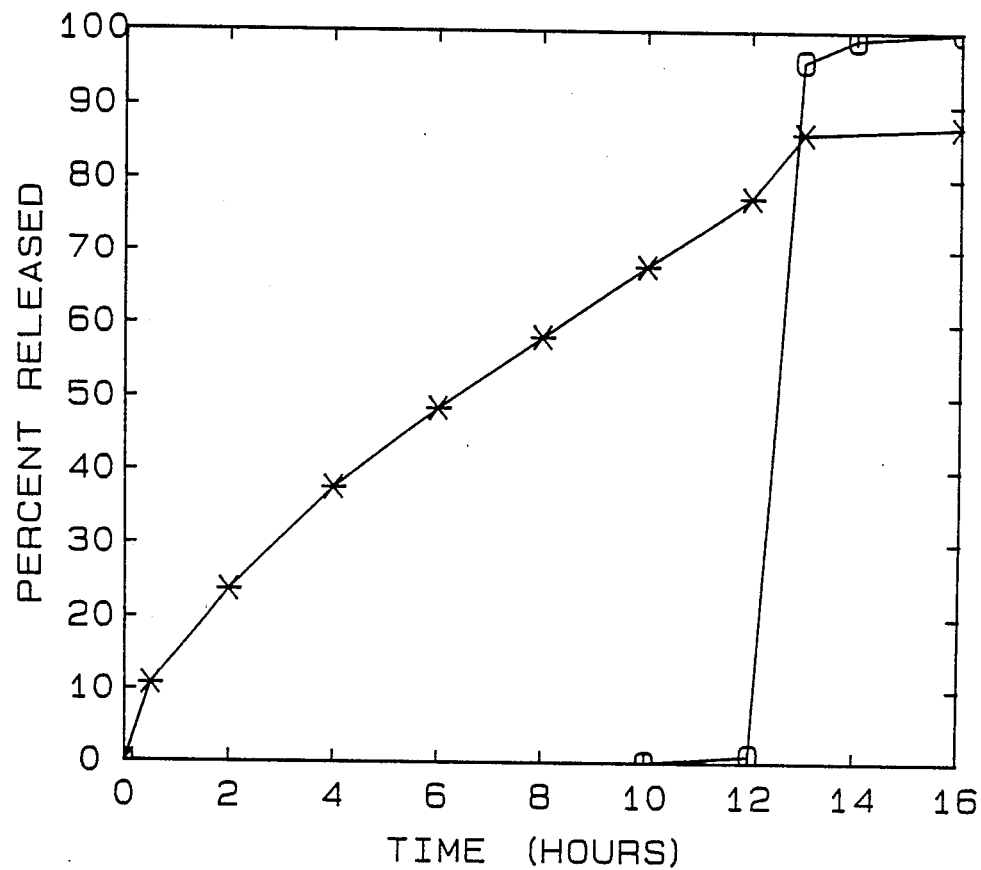
FIG. 15 is the release profile of the tablet used in Example 9.

Also the release of indomethacin was followed in pH 3 HCl by monitoring the absorbance at 365 nm (*) in the IPM layer and sodium chloride (o) (osmotic agent) by conductance. The results are shown in FIG. 15. This example shows that the system is able to deliver a lipid insoluble but lipid wettable drug substance released as a suspension in the lipid carrier.

EXAMPLE 10

Figure 16:
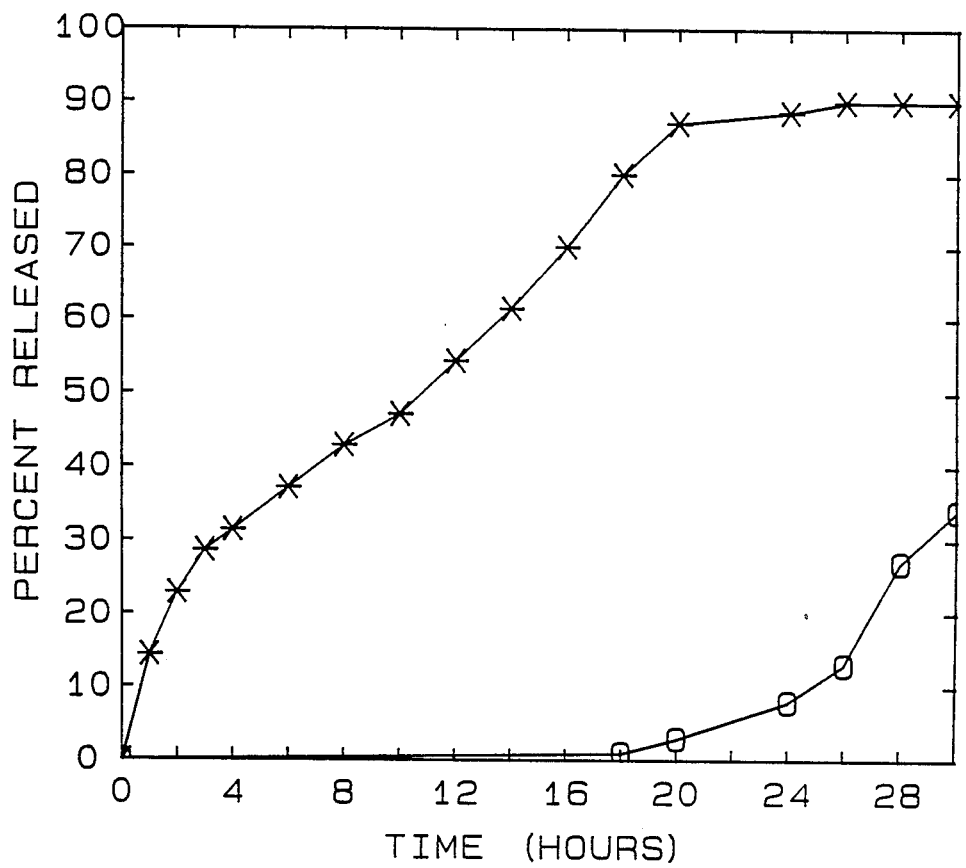
FIG. 16 is the release profile of the tablet used in Example 10.

Tablets (see FIG. 2) were prepared according to the procedure of Example 1, wherein the conditions were as described except that 48 g of Witepsol ® H-35, 12 g of Witepsol ® E-76, 40 g of sodium chloride, 2 g cyclobenzaprine free base and 0.14 g of scarlet red make up the core granules. Five grams of sodium carbonate powder was then added and mixed before tableting. Coating Solutions C and D were applied as described in Example 7. The release of scarlet red (*) (lipid carrier and cyclobenzaprine) and sodium chloride (o) (osmotic agent) are presented in FIG. 16.

EXAMPLE 11

Tablets (see FIG. 2) were prepared according to the procedure of Example 1, wherein the conditions were as described except that 3 g of indomethacin butyl ester replaced timolol as the active agent. Coating Solutions C and D were applied as described in Example 7. Solution C was sprayed at the rate 8 ml/min for 110 minutes and Solution D at 11 ml/min for 30 minutes for a total thickness of about 100μ.

Figure 17:
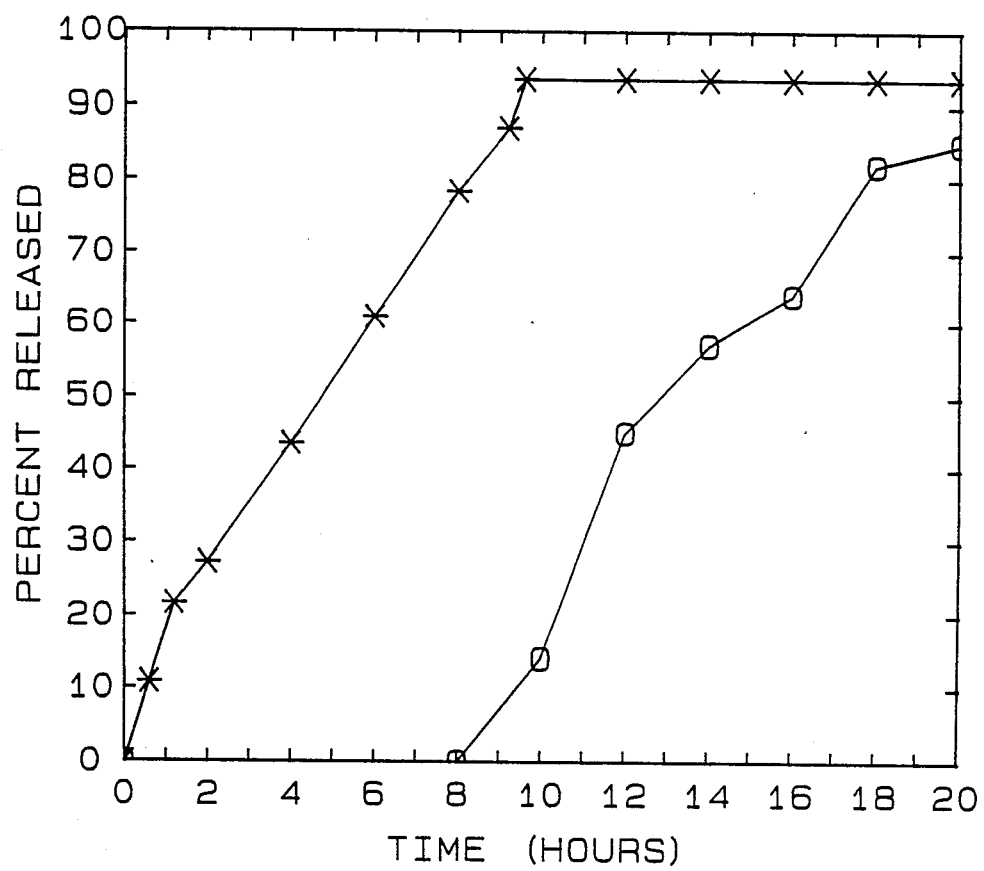
FIG. 17 is the release profile of the tablet used in Example 11.

The release profile of scarlet red (*) (lipid carrier and indomethacin butyl ester) and sodium chloride (o) (osmatic agent) are given in FIG. 17.

EXAMPLE 12

Figure 18:
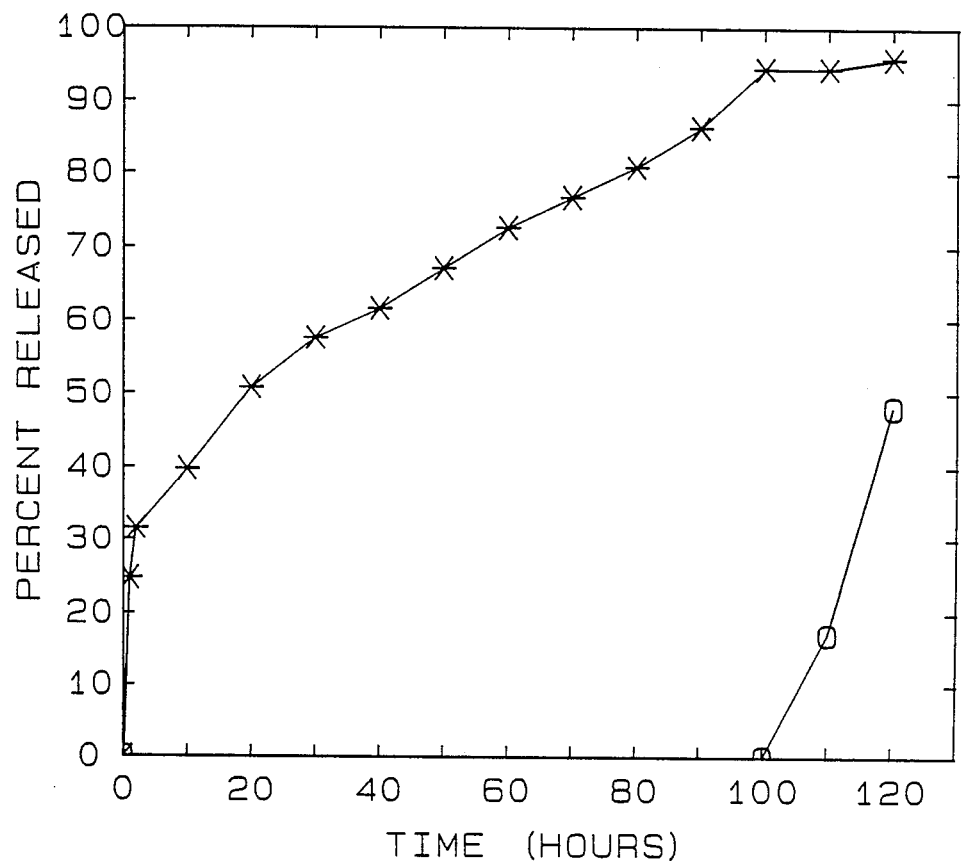
FIG. 18 is the release profile of the tablet used in Example 12.

Tablets (see FIG. 2) were prepared according to the procedure of Example 1, wherein the conditions were as described except 57 g of Witepsol ® H-35, 3 g of Witepsol ® S-55, 5 g of ibuprofen, 40 g sodium chloride and 0.14 g scarlet red made up the material. Coating Solutions C and D were described as in Example 7 and coated as described in Example 9. The release rates of scarlet red (*) (lipid carrier and ibuprofen) and sodium chloride (o) (osmotic agent) are presented in FIG. 18. The 900 ml of aqueous release media of Example 1 was adjusted to pH 3 with hydrochloric acid for use in this example.

EXAMPLE 13

Tablets (see FIG. 2) were prepared according to the procedure of Example 1, wherein the conditions were as described except that coating Solution A contained 20 g of cellulose acetate butyrate (Eastman 553-0.4) and 5 g of polyethylene glycol 400 and was sprayed using a freon atomizer spray can onto the tablets which set on a flat surface. Both faces and edges were lightly covered. Solution B was prepared using varying amounts (0, 2, 5, 10 and 15 g) of polyethylene glycol 400 in this coating solution and 1000 ml was applied to each batch. The release of scarlet red (lipid carrier and timolol) was followed and Table III presents the effect of polyethylene glycol on the rate of release.

TABLE III

| Effect of Polyethylene Glycol 400 on the Lipid Release Rate | |
|---|---|
| Percent Polyethylene Glycol 400 in Coat | Rate of Lipid Release (mg/hour) |
| 0 | 5.5 + 1.5 |
| 10 | 14 + 3 |
| 20 | 22 + 3 |
| 33 | 49 + 4 |
| 43 | 110 + 20 |

The rate of increase in lipid release increases with the percentage of polyethylene glycol in the coat especially at the higher percentages.

EXAMPLE 14

Figure 19:
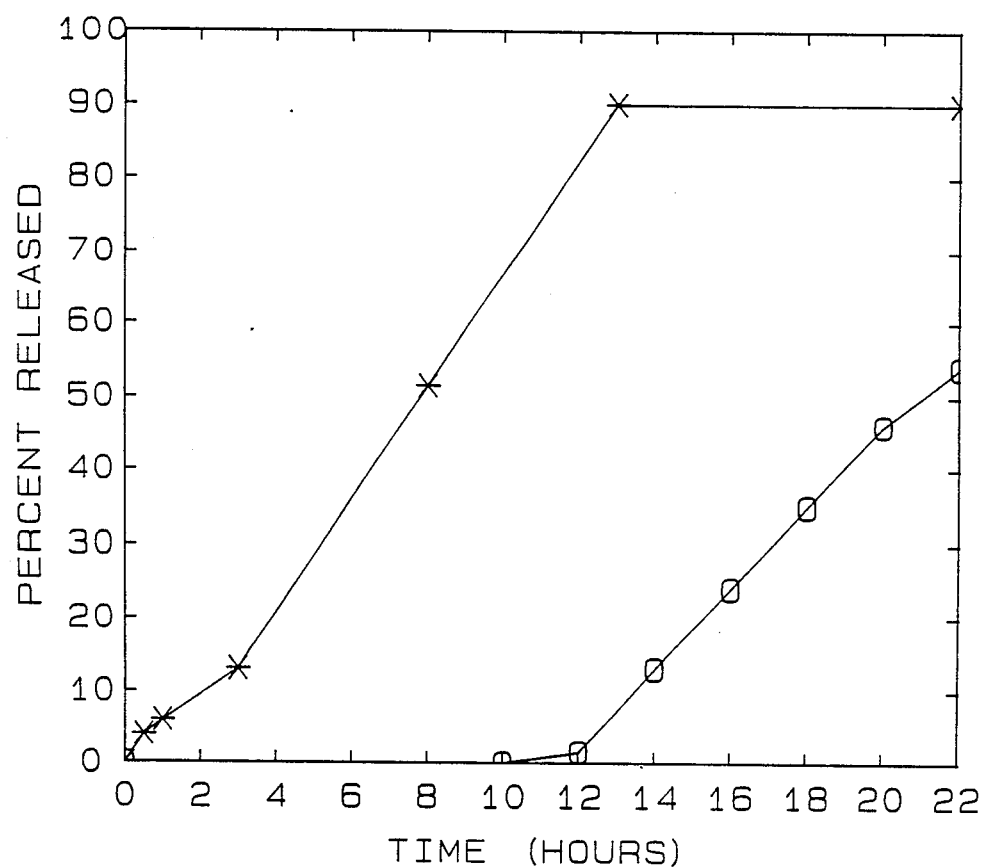
FIG. 19 is the release profile of the device used in Example 14.

A lipid osmotic device was made (see FIG. 4) as follows: A plexiglass tube of 1 cm inside diameter was cut 5 millimeters in length. A 25μ thick sheet of cellulose acetate (Eastman 436-80S) containing 12.5% by weight PEG-400 was glued with cyanoacrylate glue on one end. The cylinder was then filled with a composition consisting of 60 g of Witepsol ® H-35, 40 g of sodium chloride, 2 of timolol free base and 0.14 g of scarlet red. The system was closed by gluing a sheet of the same cellulose acetate sheeting on the remaining uncovered end. One 100μ hole was mechanically made in each of the cellulose acetate covers. The same rotation release testing device for lipid tablets was also used (FIG. 6) and the rate of release of scarlet red (*) (lipid and timolol) was measured by sampling the IPM layer and measuring the scarlet red concentration using a spectrophotometer set at 515 nm. The sodium chloride release was measured by continuously monitoring the conductance of the aqueous solution (o). The release profiles are shown in FIG. 19.

EXAMPLE 15

Figure 20:
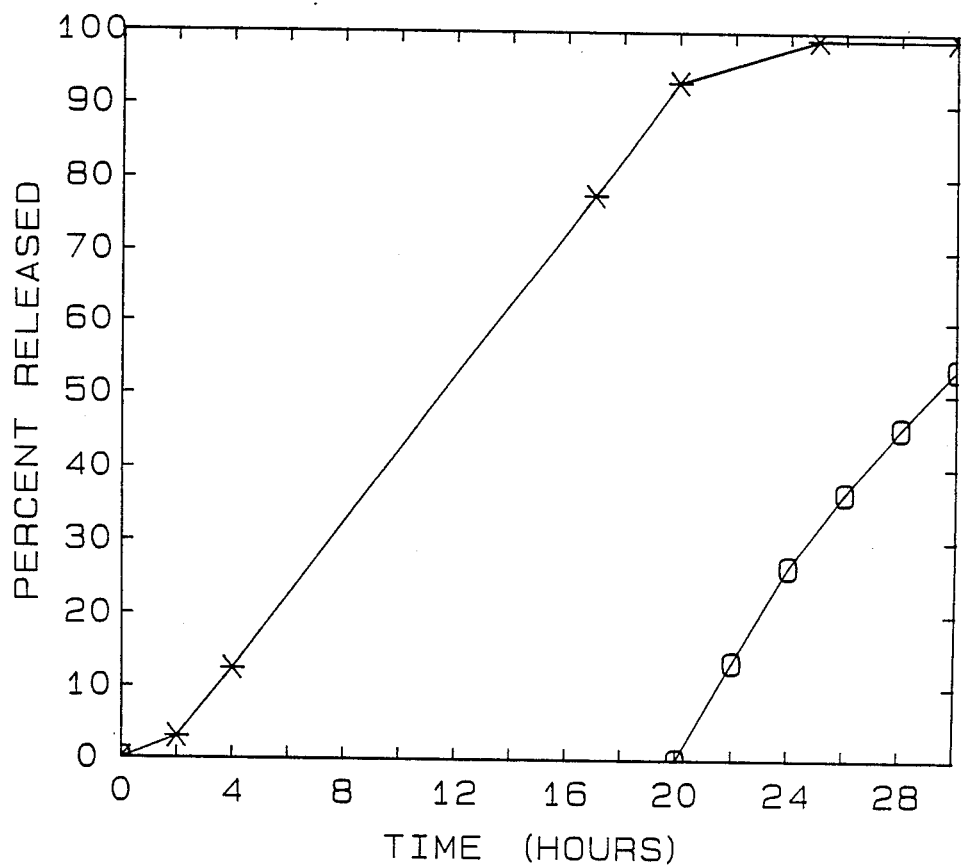
FIG. 20 is the release profile of the device used in Example 15.

A lipid osmotic device (see FIG. 4) was also made to incorporate a liquid lipid carrier. The same device as described in Example 14 was used. A 20μ thick sheet of cellulose acetate (Eastman 436-80S containing no PEG-400) was glued on one end of the cylinder. The granular sodium chloride (40 to 60 mesh) was then put in the device (200 mg) and the system was closed by gluing a sheet of the same cellulose acetate sheeting on the remaining uncovered end. The cylinder was then filled through a small hole in the cylinder wall with a composition consisting of 100 gm of a mixture of mineral oil and Captex ® 300 (medium chain triglyceride manufactured by Industrial Products Group of Stokely-Van Camp) in a ratio of 3:1 by weight and 2 g of timolol free base and 0.14 g of scarlet red. The hole was then sealed with glue. Two 100μ holes were mechanically put in the cellulose acetate films and the rate of release of scarlet red (*) (lipid and timolol) and sodium chloride (o) osmotic agent were measured as in Example 14. The release profiles are shown in FIG. 20.

EXAMPLE 16

Figure 21:
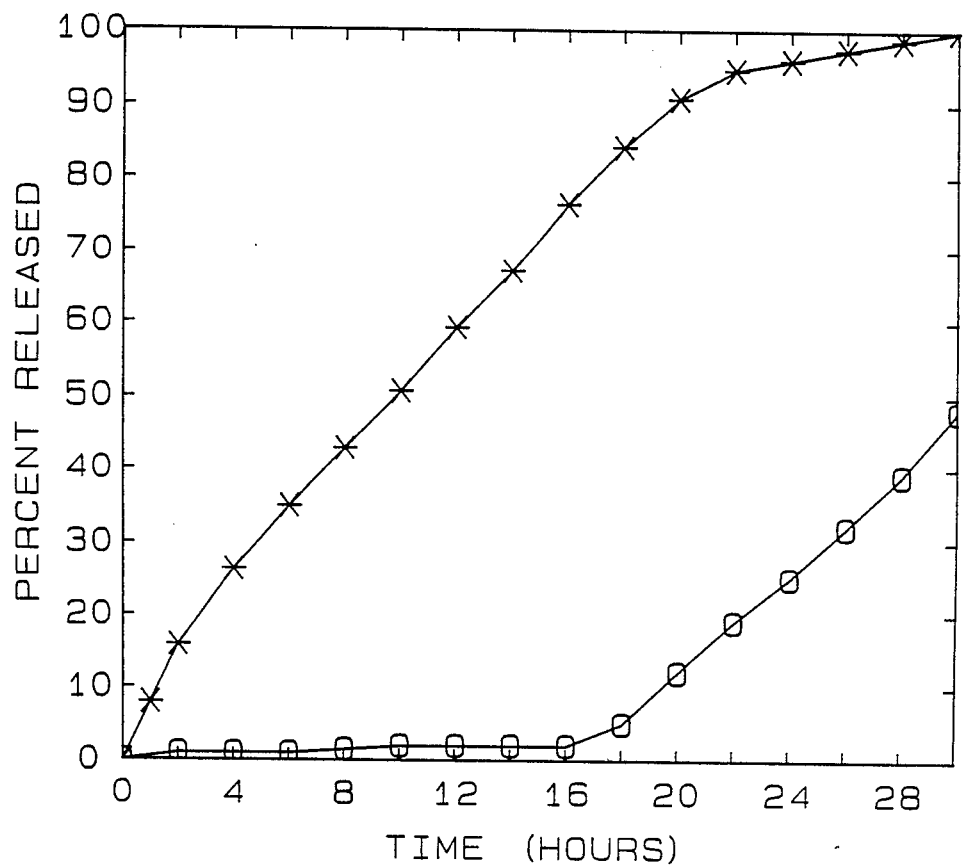
FIG. 21 is the release profile of the tablet used in Example 16.

Tablets (see FIG. 2) were prepared according to the procedure of Example 1, wherein the conditions were as described except no timolol was added. The coating Solutions C and D of Example 7 were used except that PEG 1500 was used in place of PEG-400. Solution C was coated at 11 ml/min for 85 minutes and Solution D at 11 ml/min for 15 minutes. The total coating thickness was about 125μ. The release of scarlet red (*) (lipid carrier) and sodium chloride (o) (osmotic agent) are shown in FIG. 21.

EXAMPLE 17

Figure 22:
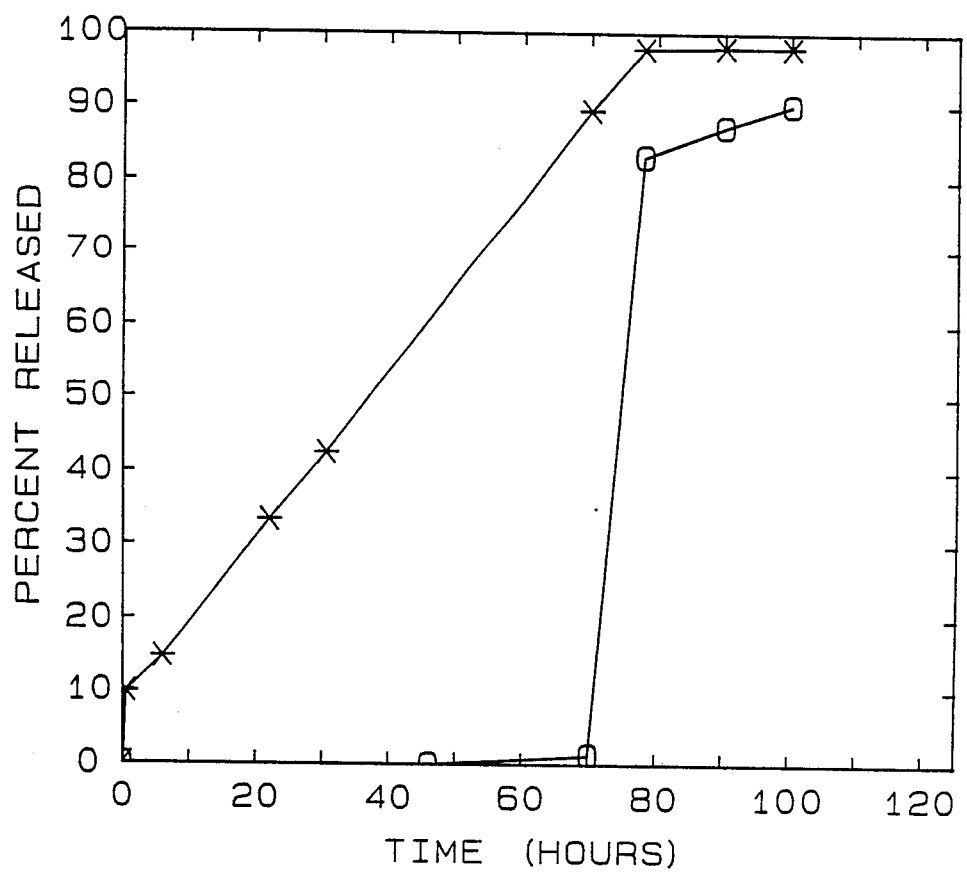
FIG. 22 is the release profile of the tablet used in Example 17.

Tablets (see FIG. 1) were prepared according to the procedure of Example 1, wherein the conditions were as described except that the only coating solution contained 1000 ml of dichloromethane, 20 g of cellulose acetate (Eastman CA-436-80S) and 5 g of diethylphthalate, the coating thickness was about 115μ. The release of scarlet red (*) (lipid carrier and timolol) and sodium chloride (o) (osmotic agent) were followed as described in Example 14. The results are shown in FIG. 22.

EXAMPLE 18

Figure 23:
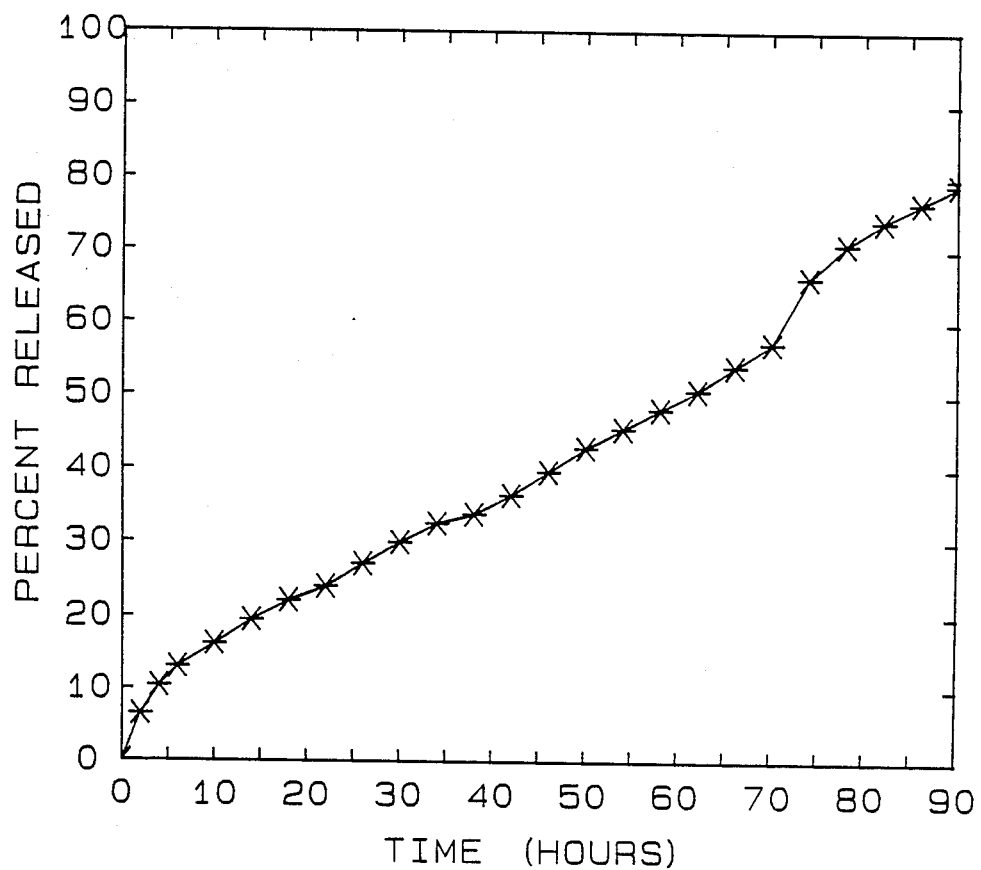
FIG. 23 is the release profile of the tablet used in Example 18.

Tablets (see FIG. 1) were prepared according to the procedure of Example 1 wherein the conditions were as described except that the coating solution consisted of 1000 ml of dichloromethane, 20 g of ethylcellulose (DOW EC-100) and 5 g of polyethylene glycol 400. The coating solution was applied at 8 ml/min for 110 minutes and 10 ml/min for 40 minutes. The coating thickness was about 120μ. The release rates were measured as described in Example 1 except 200 mg of sodium lauryl sulfate was added to the 900 ml of water in the release media. The release rate of scarlet red (*) (lipid carrier and timolol) is shown in FIG. 23. Sodium chloride release was monitored; however, none was released over the time of lipid release shown.

EXAMPLE 19

Figure 24:
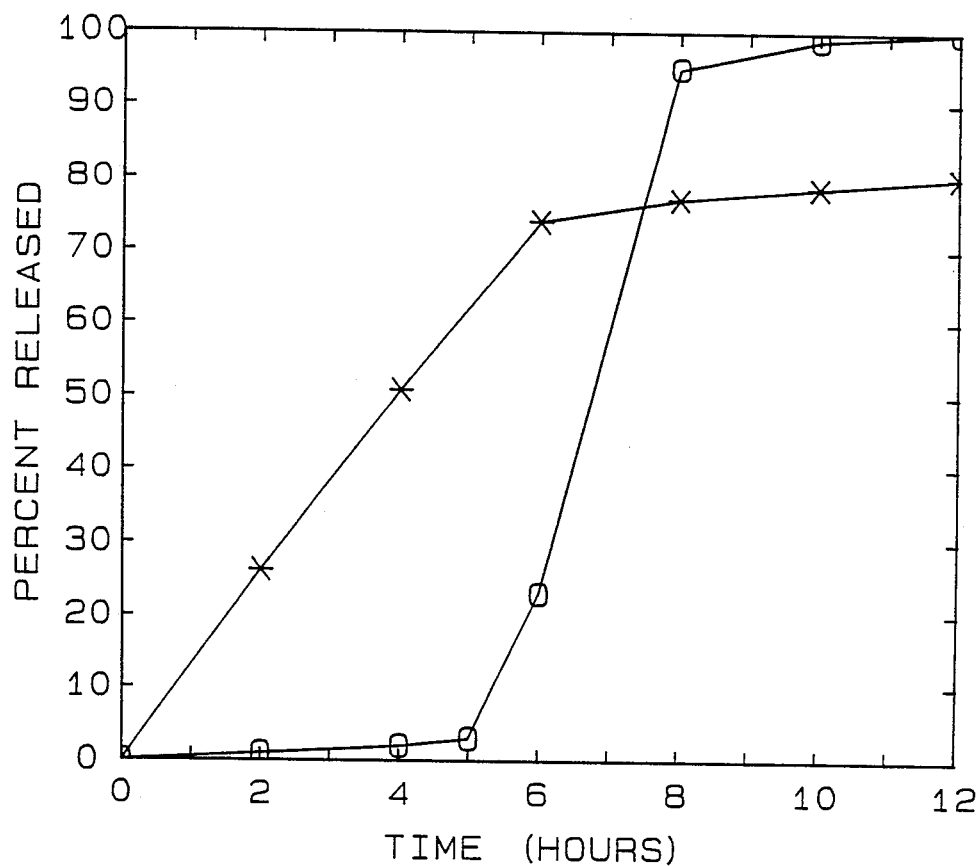
FIG. 24 is the release profile of the tablet used in Example 19.

Tablets (see FIG. 2) were prepared according to the procedure of Example 1, wherein the conditions were as described except that the coating Solution A contained 750 ml of dichloromethane, 250 methanol, 60 g of Eudragit ® (Röhm Pharma E-RS-100), and 15 g of polyethylene glycol 400. Coating Solution B contained 750 ml of dichloromethane, 250 ml of methanol, 20 g of cellulose acetate (Eastman CA-398-10), and 5 g of polyethylene glycol 400. Solution A was coated at 3 ml/min for 35 minutes and Solution B was coated at 5.1 ml/min for 45 minutes then 11 ml/min for 60 minutes. The total coating thickness was about 100μ. The release rates were measured as described in Example 1 except 200 mg of sodium laurel sulfate was added to the 900 ml of water in the release media. The release rate of scarlet red (*) (lipid carrier and timolol) and sodium chloride (o) (osmotic agent) are shown in FIG. 24.

EXAMPLE 20

Figure 25:
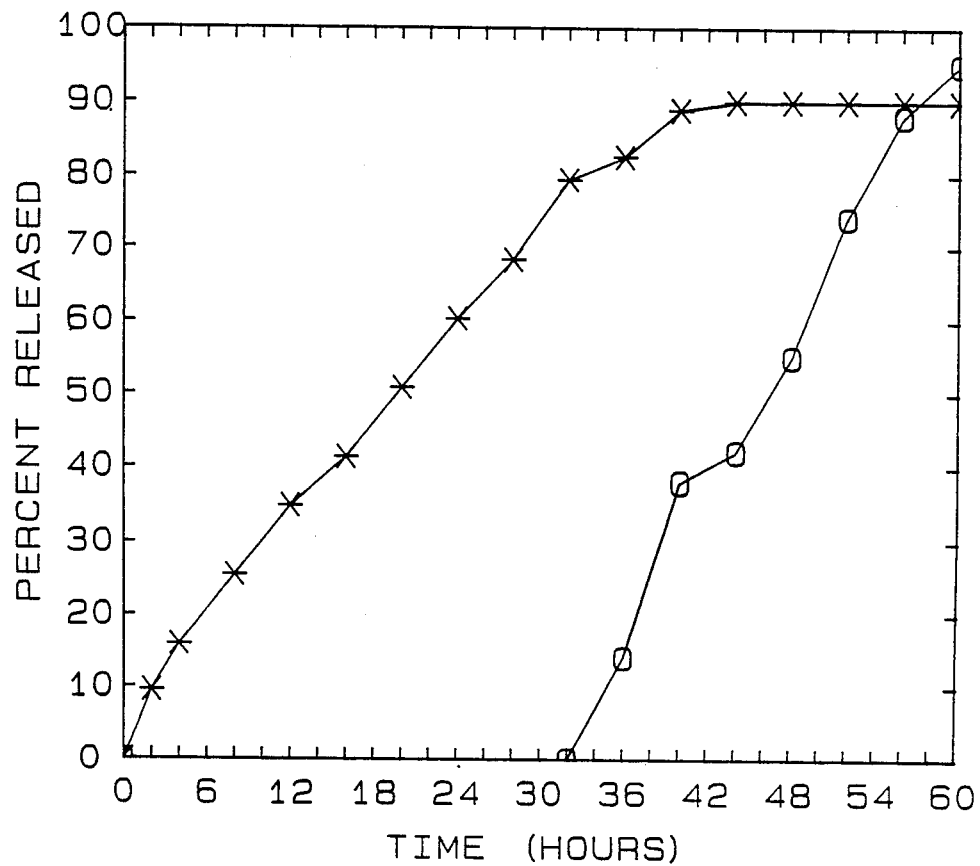
FIG. 25 is the release profile of the tablet used in Example 20.

Tablets (see FIG. 2) were prepared according to the procedure of Example 1, wherein the conditions were as described except Witepsol ® H-19 replaced the Witepsol ® H-35 in the tablet core. Tablets were coated with Solutions C and D with the same procedure as Example 7. The release rates of scarlet red (*) (lipid carrier and timolol) and sodium chloride (o) (osmotic agent) are shown in FIG. 25.

EXAMPLE 21

Figure 26:
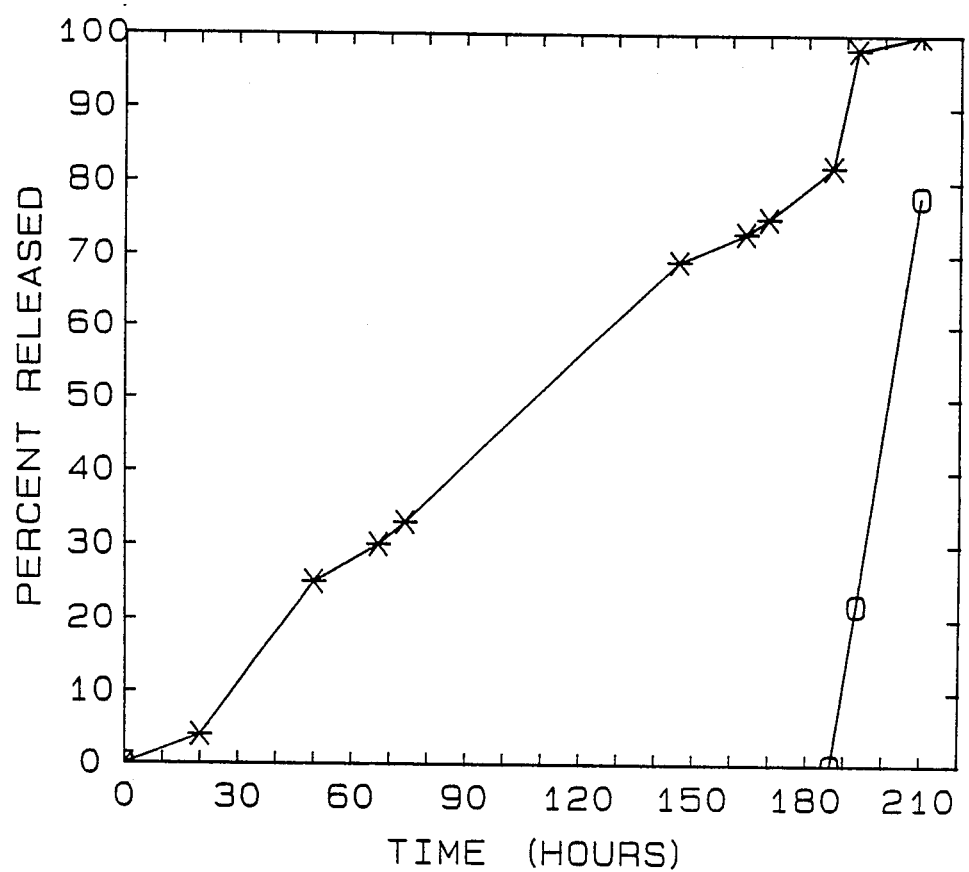
FIG. 26 is the release profile of the tablet used in Example 21.

Tablets (see FIG. 3) were prepared according to the procedure of Example 1, wherein the conditions were as described except that the coating solution was prepared as follows: 30 g of tartaric acid were dissolved in 375 ml of anhydrous methanol. This was then added to a solution of 1,125 ml of dichloromethane containing 30 g of cellulose acetate (Eastman CA-436-80S) and 7.5 g of polyethylene glycol 400. This solution was then applied to the tablets at a rate of 8 ml/min for 110 minutes. The coating thickness was about 105μ. The rates of release of scarlet red (*) (lipid carrier and timolol) and sodium chloride (o) (osmotic agent) are shown in FIG. 26. This example shows that a microporous coating can be applied to these lipid tablets such that lipid can be preferentially pumped from the tablet over the aqueous solution of the osmotic agent. The lipid was observed to be pumped from a very large number of pores over the entire surface of the tablet.

EXAMPLE 22

A multiparticulate dosage form (see FIG. 5) of the instant invention was prepared as follows: A mixture of 100 g sodium chloride (osmotic agent), milled and screened to pass a 140 mesh screen and be retained on a 170 mesh screen 150 g Witepsol ® H-35 (lipid carrier) and 0.35 g scarlet red (lipid soluble dye) were added to a 250 ml stainless steel beaker and heated to 45° C. by means of a heating tape. The beaker was modified to allow its contents to drip through a 0.030 inch orifice connected to the bottom; vigorous stirring of the molten mixture was maintained by use of a mechanically driven stirrer. The mixture was held at 45°–50° C. and allowed to drip into several liters of liquid nitrogen to form individual spherical beads upon rapid cooling of the droplet. Stirring was also maintained in the liquid nitrogen collection vessel. The resultant beads were collected by decanting the liquid nitrogen and were allowed to slowly warm to room temperature over several hours in a low-humidity environment. The beads were spherical in shape and over 90%, on a weight basis, fell in the size range of 1.5 to 2.5 mm diameter, by this process. Following this procedure, a batch of beads was prepared from a mixture of 66.7 g sodium chloride (osmotic agent), milled and screened to pass a 80 mesh screen and be reatined on a 140 mesh screen, 100 g Witepsol ® H-35 (lipid carrier) and 5 g indomethacin butyl ester (active agent). The resultant beads were white in color and spherical in shape; over 90% by weight were in the size range of 1.5 to 2.5 mm diameter.

A microporous cellulose triacetate coating was applied to the beads as follows: A 45 g portion of the beads containing scarlet red and a 30 g portion of the beads containing indomethacin butyl ester were placed in a Uni-Glatt ® fluidized bed coater equipped with a 4 inch Wurster coating column. The beads were easily distinguished by their color. They were coated with a solution prepared from 50 g cellulose triacetate (Eastman CA-436-80S), 12.5 g polyethylene glycol 400 (plasticizer and flux enhancing agent), 50 g tartaric acid (water soluble pore-former), 750 ml dichloromethane, and 250 ml methanol. The coating solution was applied for a period of 20 minutes at a flow rate of 15 ml/min with 2 atmospheres of atomization air pressure to the spray gun. The beads were maintained in a fluidized state in the coating column with a moderate flow of unheated, ambient air. After drying in the unit, the coated beads were collected; they were still easily differentiated by their color; appropriate numbers of red beads, containing scarlet red, and white beads, containing indomethacin butyl ester, were separated for testing. The beads had a coating thickness of approximately 100μ.

Figure 27:
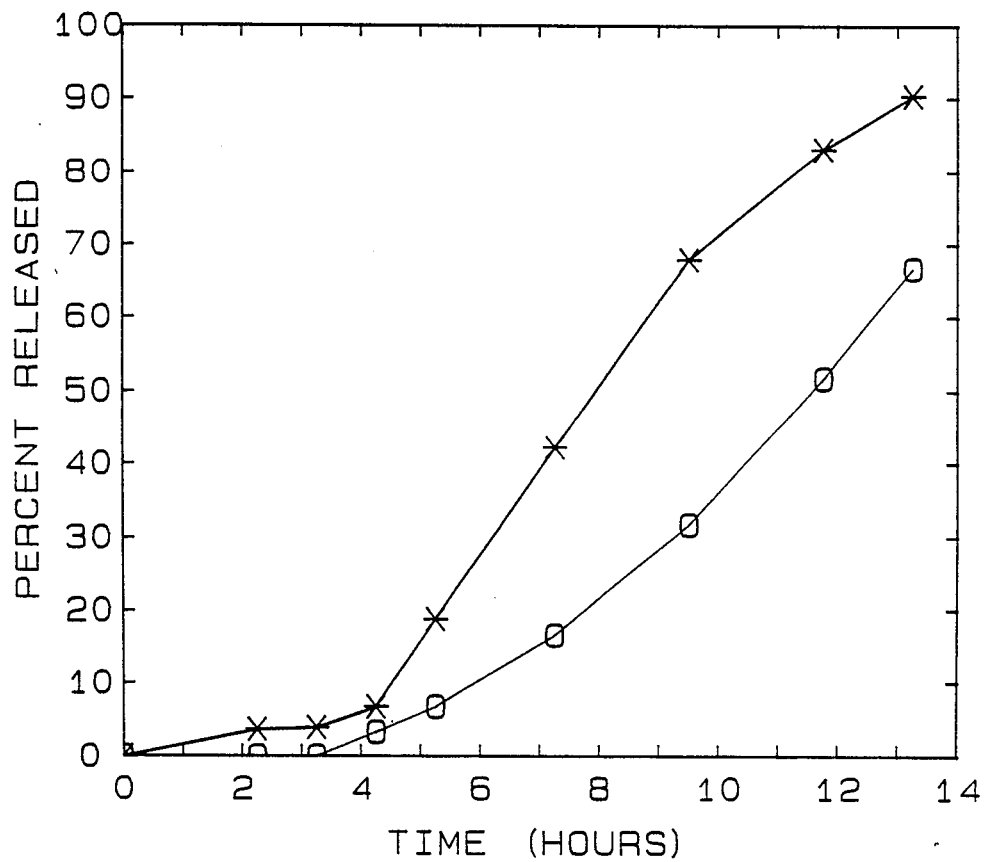
FIG. 27 is the release profile of the multiparticulate dosage form used in Example 22.
Figure 28:
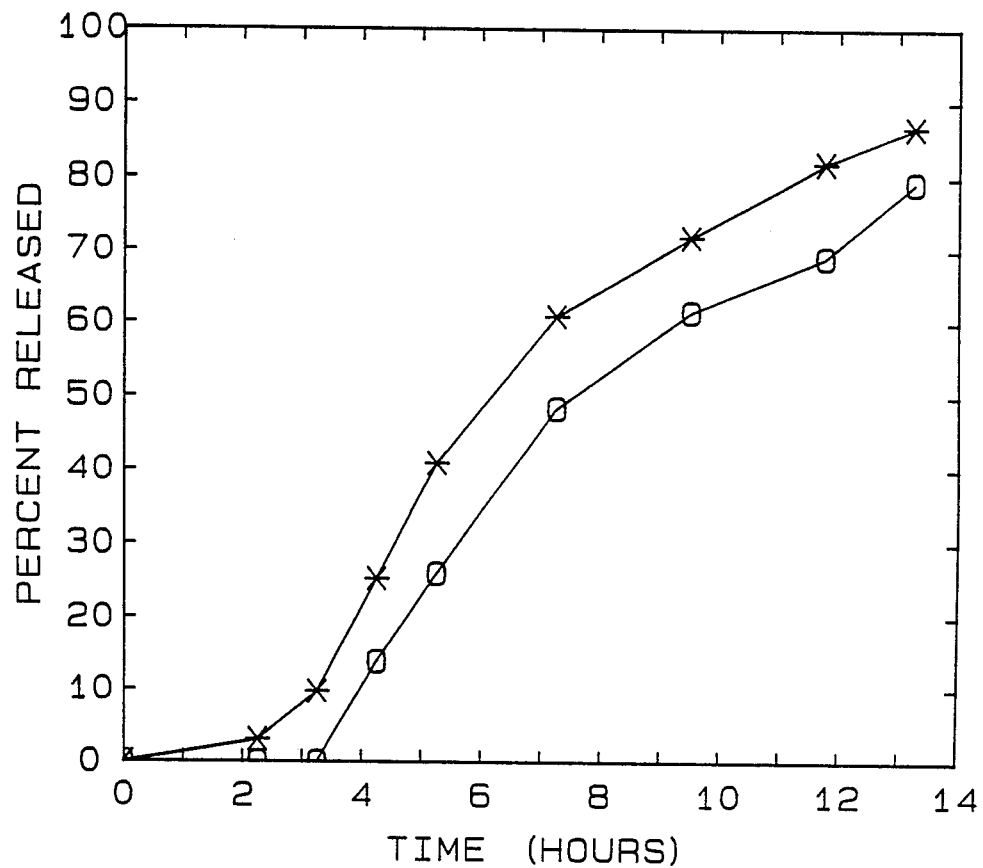
FIG. 28 is the release profile of the multiparticulate dosage form used in Example 22.

The in vitro release rates of scarlet red and indomethacin butyl ester from these coated bead preparations were determined by a modification of the USP Paddle dissolution method: 900 ml of water at 37° C., stirred at 100 rpm, with 50 ml of an isopropyl myristate (IPM) upper layer. Fifty coated beads, weighing a total of 364 mg, containing scarlet red, were added to one flask and 50 coated beads, weighing a total of 329 mg, containing indomethacin butyl ester, were added to a separate dissolution flask. Subsequent to the addition of the beads to the flasks, 50 ml of IPM was added to each flask to aid in analysis of the lipid-soluble dye or active agent to be release from the beads. These samples of coated beads are typical of the amounts commonly filled in hard gelatin capsules for oral administration. FIG. 5 depicts a hard gelatin capsule, (31) filled with microporous-coated beads, (30). Each bead is comprised of a microporous coating, (29) and a core containing osmotic agent, (28) in a lipid carrier, (27) containing the active agent. The coated beads are released to the gastrointestinal tract upon the capsule shell dissolving. The rates of release of scarlet red and indomethacin butyl ester from these two microporous-coated bead preparations were determined by measuring the absorbance of the IPM layer in the dissolution flasks at 514 nm (scarlet red) or at 320 nm (indomethacin butyl ester). The release of sodium chloride was determined by measurement of the conductance of the dissolution media with a dip-type conductance cell periodically during the release process. Prior to each sampling, the coated beads were stirred more vigorously for a few seconds to dislodge any lipid droplets clinging to their outer surfaces. After 13.25 hours, the coated beads were crushed within the dissolution flasks to release any remaining contents. A final sample, subsequent to crushing of the coated beads, established the total content assay value; amounts released at intermediate times are expressed as percentages of the total content assay and are shown in FIGS. 27 and 28 as plots of percentage scarlet red (*) indomethacin butyl ester (*), or sodium chloride (o) (osmotic agent) released versus time.

What is claimed is:

1. A lipid osmotic pump, for the controlled delivery of a substantially water insoluble active agent into an aqueous environment, comprising:
(A) a core, comprising an admixture of:
  (i) a beneficial amount of at least one substantially water insoluble active agent which is lipid soluble and/or lipid wettable;
  (ii) a sufficient amount of at least one water immiscible lipid carrier, which is liquid at the temperature of intended use, to dissolve and/or suspend said active agent; and
  (iii) a sufficient amount of at least one osmotic agent to ensure release of said lipid carrier from the pump; and
(B) surrounded by a water insoluble wall;
  (i) having a thickness of about 1 to 1000 microns;
  (ii) which is preferentially wetted by said lipid carrier over an aqueous solution of said osmotic agent;
  (iii) having a water permeability of about $1 \times 10^{-18}$ to $4 \times 10^{-15}$ cm$^3$ sec/g;
  (iv) prepared from atleast some polymer permeable to waster but substantially impermeable to said osmotic agent; and
  (v) having a means for said active agent to be released through said water insoluble wall;
(C) wherein at the temperature of use, the lipid carrier is liquid and retains the lipid soluble or lipid wettable agent in a dissolved or suspended state so that upon the dissolution of the osmotic agent in the imbibed water the lipid carrier and the dissolved or suspended active agent is released from the osmotic pump at a controlled rate.

2. The lipid osmotic pump of claim 1, wherein said means for said active agent to be released through said water insoluble wall is a hole connecting said core with the exterior of said water insoluble wall.

3. The lipid osmotic pump of claim 1, wherein said water insoluble wall is microporous and, thus, provides a means for said active agent to be released through said water insoluble wall.

4. The lipid osmotic pump of claim 1, wherein said microporous, water impermeable, wall is made by dispersing throughout said wall 5 to 100 parts of pore forming additive per 150 parts wall polymer.

5. The lipid osmotic pump of claim 4, wherein said pore forming additive is selected from the group consisting of alkali metal salts, alkaline earth metal salts, transition metal salts, organic acids, saccharides, and organic polyols.

6. The lipid osmotic pump of claim 3, wherein said microporous, water insoluble, wall is made by a process selected from the group consisting of etched nuclear tracking, solvent evaporation gas formation, cold stretching, hot stretching, solvent leaching, ion exchange reaction, and polyelectrolyte processes.

7. The lipid osmotic pump of claim 1, wherein said water insoluble wall is comprised of at least two different polymer layers with the polymer closest to the core being preferentially wetted by said lipid carrier over an aqueous solution of said osmotic agent.

8. The lipid osmotic pump of claim 1, wherein said lipid carrier is a liquid at 37° C.

9. The lipid osmotic pump of claim 1, wherein said lipid carrier is selected from the group consisting of triglycerides, cocoa butter, hard butter, mineral oil, petrolatum-mineral oil mixtures, saqualine, fluorocarbons, fatty acids, their esters and mixtures thereof.

10. The lipid osmotic pump of claim 1, wherein said water insoluble wall further comprises plasticizer and flux regulating additives.

11. The lipid osmotic pump of claim 10, wherein 5 to 100 parts of plasticizer and flux regulating additives, per 100 parts wall polymer, are used.

12. The lipid osmotic pump of claim 1, wherein said polymer used to prepare said water insoluble wall is selected from the group consisting of cellulose acetate, cellulose diacetate, cellulose triacetate, cellulose acetate propionate, and cellulose acetate butyrate.

13. The lipid osmotic pump of claim 1, wherein said water insoluble wall has a thickness of 50 to 300 microns.

14. The lipid osmotic pump of claim 1, wherein said active agent is 1 µg to 5 g of at least one drug.

15. The lipid osmotic pump of claim 1, wherein 5 mg to 5 g of said lipid carrier is used.

16. The lipid osmotic pump of claim 1, wherein said osmotic agent is a water soluble active agent.

17. A water soluble capsule containing at least two osmotic pumps of claim 1.

18. The lipid osmotic pump of claim 1, wherein said core is a single compartment.

19. The lipid osmotic pump of claim 1, wherein in operation said osmotic agent is expelled, substantially subsequent to said lipid carrier.

* * * * *